United States Patent
Dubois et al.

(10) Patent No.: US 8,399,491 B2
(45) Date of Patent: Mar. 19, 2013

(54) DERIVATIVES OF INDOLE-2-CARBOXAMIDES AND OF AZAINDOLE-2-CARBOXAMIDES SUBSTITUTED WITH A SILANYL GROUP, PREPARATION THEREOF AND THERAPEUTIC USE THEREOF

(75) Inventors: Laurent Dubois, Paris (FR); Yannick Evanno, Paris (FR); André Malanda, Paris (FR)

(73) Assignee: Sanofi, Paris (FR)

( * ) Notice: Subject to any disclaimer, the term of this patent is extended or adjusted under 35 U.S.C. 154(b) by 180 days.

(21) Appl. No.: 12/840,665

(22) Filed: Jul. 21, 2010

(65) Prior Publication Data
US 2011/0009365 A1    Jan. 13, 2011

Related U.S. Application Data

(63) Continuation of application No. PCT/FR2009/000054, filed on Jan. 20, 2009.

(30) Foreign Application Priority Data

Jan. 23, 2008 (FR) ...................... 08 00343

(51) Int. Cl.
*A61K 31/4427* (2006.01)
*C07D 401/06* (2006.01)
(52) U.S. Cl. .................. 514/339; 546/268.1; 546/276.4; 546/278.1; 548/465; 514/336
(58) Field of Classification Search ............... 546/268.1, 546/276.4, 278.1; 548/465; 514/336, 339, 514/415
See application file for complete search history.

(56) References Cited

U.S. PATENT DOCUMENTS

| | | | | |
|---|---|---|---|---|
| 7,786,104 B2 * | 8/2010 | DuBois et al. | ............. | 514/210.2 |
| 8,153,650 B2 * | 4/2012 | Dubois et al. | ................. | 514/299 |

FOREIGN PATENT DOCUMENTS

| | | |
|---|---|---|
| WO | 03/068749 A1 | 8/2003 |
| WO | 2005/032493 A2 | 4/2005 |
| WO | 2005/072681 A2 | 8/2005 |
| WO | 2007/010144 A1 | 1/2007 |

OTHER PUBLICATIONS

International Search Report issued in International application No. PCT/FR2009/000054 dated Jul. 27, 2009.

\* cited by examiner

*Primary Examiner* — Golam M M Shameem
(74) *Attorney, Agent, or Firm* — Scully, Scott, Murphy & Presser, P.C.

(57) ABSTRACT

This disclosure relates to compounds of formula (I):

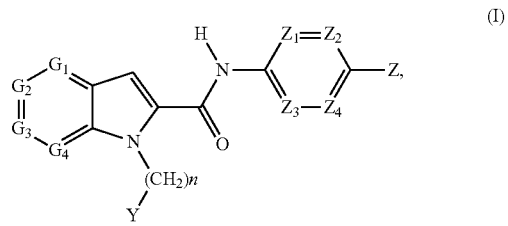

wherein $G_1$, $G_2$, $G_3$, $G_4$, n, Y, Z, $Z_1$, $Z_2$, $Z_3$, and $Z_4$ are as defined in the disclosure, or a salt thereof, or a hydrate or solvate thereof, and to processes for the preparation of these compounds and the therapeutic use thereof.

17 Claims, No Drawings

DERIVATIVES OF INDOLE-2-CARBOXAMIDES AND OF AZAINDOLE-2-CARBOXAMIDES SUBSTITUTED WITH A SILANYL GROUP, PREPARATION THEREOF AND THERAPEUTIC USE THEREOF

The subject of the invention is compounds derived from indole-2-carboxamides and from azaindole-2-carboxamides substituted with a silanyl group, which exhibit an antagonistic or agonistic activity, in vitro and in vivo, with respect to TRPV1 (or VR1) receptors.

A first subject of the invention concerns the compounds corresponding to general formula (I) below.

Another subject of the invention concerns processes for preparing the compounds of general formula (I).

Another subject of the invention concerns the use of the compounds of general formula (I), in particular in medicaments or in pharmaceutical compositions.

The compounds of the invention correspond to general formula (I):
in which:

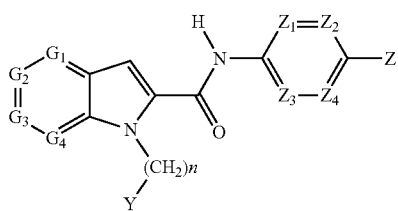

(I)

$G_1$, $G_2$, $G_3$ and $G_4$ are, independently of one another, a C—X group or a nitrogen atom;

X is chosen from a hydrogen atom, a halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, $NR_1R_2$, aryl-$C_1$-$C_6$-alkylene-O, aryl, heteroaryl or —Si($X_1$)($X_2$)($X_3$) group; the $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkoxyl and $C_3$-$C_7$-cycloalkyl-$C_1$-$C_6$-alkylene-O— groups being optionally substituted with a hydroxyl, $C_1$-$C_6$-alkoxyl or $NR_4R_5$ group; the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

one of $G_1$, $G_2$, $G_3$ and $G_4$ and at most one of $G_1$, $G_2$, $G_3$ and $G_4$ is a C—X group where X is an —Si($X_1$)($X_2$)($X_3$) group;

$X_1$, $X_2$ and $X_3$ are, independently of one another, a $C_1$-$C_6$-alkyl, $C_3$-$C_7$-cycloalkyl, $C_3$-$C_7$-cycloalkyl-$C_1$-$C_6$-alkyl, hydroxyl, aryl or heteroaryl group;

the aryl or heteroaryl groups of $X_1$, $X_2$, $X_3$ being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

the $C_1$-$C_6$-alkyl, $C_3$-$C_7$-cycloalkyl and $C_3$-$C_7$-cycloalkyl-$C_1$-$C_6$-alkyl groups of $X_1$, $X_2$, $X_3$ being optionally substituted with one or more substituents chosen from a hydroxyl, $C_1$-$C_6$-alkoxyl, aryl-O—, $NR_1R_2$, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

it also being possible for $X_1$ and $X_2$ to form, together with the silicon atom which bears them, a 4- to 7-membered ring optionally containing a heteroatom chosen from O, S and N;

n is equal to 0, 1, 2 or 3;

Y is an aryl or a heteroaryl; the aryl or the heteroaryl being optionally substituted with one or more substituents chosen from a halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, thiol, —S(O)—$C_1$-$C_6$-alkyl, —S(O)$_2$—$C_1$-$C_6$-alkyl, C(O)$NR_1R_2$, SO$_2NR_1R_2$, SF$_5$, nitro, OCON$R_1R_2$, $NR_3COR_4$, $NR_3CONR_1R_2$, $NR_1R_2$, $NR_3SO_2NR_1R_2$, $NR_3COR_4$, $NR_3SO_2R_5$, aryl-$C_1$-$C_6$-alkylene or aryl group; the aryl and the aryl-$C_1$-$C_6$-alkylene being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$Z_1$, $Z_2$, $Z_3$, $Z_4$ are, independently of one another, a nitrogen atom or a C($R_6$) group, at least one corresponding to a nitrogen atom and at least one corresponding to a C($R_6$) group; the nitrogen atom or one of the nitrogen atoms present in the ring, defined as nitrogen of position 1, being optionally substituted with $R_7$ when the carbon atom at position 2 or 4 relative to this reference nitrogen is substituted with an oxo or thio group;

Z is either a cyclic amine linked via the nitrogen atom, of formula:

in which:

A is a $C_1$-$C_7$alkylene group optionally substituted with one or two $R_8$ groups;

B is a $C_1$-$C_7$alkylene group optionally substituted with one or two $R_9$ groups;

L is a bond, or a sulphur, oxygen or nitrogen atom; the nitrogen atom being optionally substituted with an $R_{10}$ or $R_{11}$;

the carbon atoms of the cyclic amine Z being optionally substituted with one or more $R_{12}$ groups which may be identical to or different from one another;

or an acyclic amine, linked via the nitrogen atom, of formula NRaRb in which Ra and Rb are, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-alkyl-C(O)—, HO—C(O)—$C_1$-$C_6$-alkylene, $C_1$-$C_6$-alkyl-O—C(O)—$C_1$-$C_6$-alkylene, aryl or heteroaryl group, it being possible for Ra and Rb to be optionally substituted with one or more Rc groups which may be identical to or different from one another;

Rc is a halogen atom, or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, cyano, C(O)$NR_1R_2$, $NR_1R_2$, SO$_2NR_1R_2$, $NR_3COR_4$, $NR_3SO_2R_5$, OC(O)$NR_1R_2$, $NR_3COOR_5$, $NR_3CONR_1R_2$, $NR_3SO_2NR_1R_2$, hydroxyl, thiol, oxo, thio, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ are, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group; or $R_1$ and $R_2$ form, together with the nitrogen atom which bears them, an azetidinyl, pyrrolidinyl, piperidinyl, azepinyl, morpholinyl, thiomorpholinyl, piperazinyl or homopiperazinyl group, this group being optionally substituted with a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_3$ and $R_4$ are, independently of one another,
a hydrogen atom or a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
or $R_3$ and $R_4$ together form a $(C_2$-$C_5)$alkylene group;
or $R_1$ and $R_3$ together form a $(C_2$-$C_5)$alkylene group;

$R_5$ is a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
or $R_3$ and $R_5$ together form a $(C_2$-$C_5)$alkylene group;

$R_6$ is a hydrogen or halogen atom, or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, hydroxyl, thiol, oxo, thio, aryl, aryl-$C_1$-$C_6$-alkylene or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_7$ is a hydrogen atom, or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, aryl, aryl-$C_1$-$C_6$-alkylene or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_8$, $R_9$ and $R_{10}$ are defined such that:
two $R_8$ groups may together form a bond or a $C_1$-$C_6$-alkylene group;
two $R_9$ groups may together form a bond or a $C_1$-$C_6$-alkylene group;
$R_8$ and $R_9$ may together form a bond or a $C_1$-$C_6$-alkylene group;
$R_8$ and $R_{10}$ may together form a bond or a $C_1$-$C_6$-alkylene group;
$R_9$ and $R_{10}$ may together form a bond or a $C_1$-$C_6$-alkylene group;

$R_{11}$ is a hydrogen atom, or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, hydroxyl, $C_1$-$C_6$-alkyl-CO—, COOR$_5$, C(O)NR$_1$R$_2$, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group;

$R_{12}$ is a fluorine atom, a $C_1$-$C_6$-alkyl group optionally substituted with an $R_{13}$ group; $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-cycloalk-1,1-diyl, $C_3$-$C_7$-heterocycloalk-1,1-diyl optionally substituted on a nitrogen atom with an $R_{11}$ group; $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, CO$_2$H, C(O)O—$C_1$-$C_6$-alkyl, C(O)NR$_1$R$_2$, NR$_1$R$_2$, NR$_3$COR$_4$, OC(O)NR$_1$, R$_2$, NR$_3$COOR$_5$, NR$_3$CONR$_1$R$_2$, hydroxyl, thiol, oxo, thio, aryl-$C_1$-$C_6$-alkylene or aryl; the aryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group;

$R_{13}$ is a $C_1$-$C_6$-alkoxyl, $C_3$-$C_7$-cycloalkoxyl, $C_3$-$C_7$-cycloalkyl-$C_1$-$C_6$-alkylene-O—, C(O)NR$_1$R$_2$, NR$_1$R$_2$, NR$_3$COR$_4$, OC(O)NR$_1$R$_2$, NR$_3$COOR$_5$ or hydroxyl group.

In the compounds of general formula (I), the nitrogen atom(s) may be in oxidized form (N-oxide).

By way of nonlimiting examples of substituted or unsubstituted amines Z, mention may be made of methylamine, ethylamine, 2-methoxyethylamine, 2-hydroxyethylamine, cyclopropylamine, hydroxylamine, 2-(N,N-dimethylamino)ethylamine, dimethylamine, isopropylamine, N-ethylmethylamine, 2,5-dimethylpyrrolidine, 3-hydroxypyrrolidine, 3-ethoxypyrrolidine, 3,3-difluoropyrrolidine, 3,3-difluoroazetidine, 3-hydroxyazetidine, proline, aziridine, azetidine, pyrrolidine, piperidine, azepine, morpholine, thiomorpholine, piperazine, homopiperazine, azabicyclo[3.1.0]hexanes, azabicyclo[3.2.0]heptanes, azabicyclo[3.3.0]octanes, octahydrofuropyrroles, octahydropyrrolopyrroles, octahydroindole, octahydroisoindole, octahydropyrrolopyridines, decahydroquinoline, decahydroisoquinoline, decahydronaphthyridines, octahydropyridopyrazine, azabicyclo[3.1.1]heptanes, diazabicyclo[2.2.1]heptanes, azabicyclo[3.2.1]octanes, diazabicyclo[3.2.1]octanes and azabicyclo[3.3.1]nonanes.

In the context of the present invention:
the expression "$C_t$—$C_z$ where t and z may have the values of 1 to 7" is intended to mean a carbon-based chain that may contain from t to z carbon atoms; for example, "$C_1$-$C_3$" is intended to mean a carbon-based chain that may contain from 1 to 3 carbon atoms;
the term "an alkyl" is intended to mean: a linear or branched, saturated aliphatic group. By way of examples, mention may be made of methyl, ethyl, propyl, isopropyl, butyl, isobutyl, tert-butyl, pentyl, etc., groups;
the term "an alkylene" is intended to mean: a linear or branched, saturated divalent alkyl group, for example a $C_{1-3}$-alkylene group is a linear or branched, divalent carbon-based chain containing from 1 to 3 carbon atoms, for example a methylene, ethylene, 1-methylethylene or propylene;

the term "a cycloalkyl" is intended to mean: a cyclic carbon-based group. By way of examples, mention may be made of cyclopropyl, cyclobutyl, cyclopentyl, cyclohexyl, etc., groups;

the term "a heterocycloalkyl" is intended to mean: a 3- to 7-membered cyclic group containing from 1 to 2 heteroatoms chosen from O, S or N;

the term "a cycloalk-1,1-diyl" or "a heterocycloalk-1,1-diyl" is intended to mean: a group of the type:

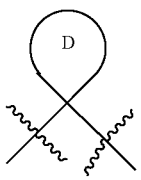

where D is a cycloalkyl or heterocycloalkyl group;

the term "a fluoroalkyl" is intended to mean: an alkyl group of which one or more hydrogen atoms has (have) been substituted with a fluorine atom;

the term "an alkoxyl" is intended to mean: an —O-alkyl radical where the alkyl group is as defined above;

the term "a cycloalkoxyl" is intended to mean: an —O-cycloalkyl radical where the cycloalkyl group is as defined above;

the term "a fluoroalkoxyl" is intended to mean: an alkoxyl group of which one or more hydrogen atoms has (have) been substituted with a fluorine atom;

the term "a thioalkyl" is intended to mean: an —S-alkyl radical where the alkyl group is as defined above;

the term "an aryl" is intended to mean: a cyclic aromatic group comprising between 6 and 10 carbon atoms. By way of examples of aryl groups, mention may be made of phenyl or naphthyl groups;

the term "a heteroaryl" is intended to mean: a 5- to 14-membered aromatic monocyclic, bicyclic or tricyclic group containing from 1 to 8 heteroatoms chosen from O, S or N.

By way of examples of a monocyclic heteroaryl, mention may be made of imidazolyl, pyrazolyl, thiazolyl, oxazolyl, isothiazolyl, isoxazolyl, furanyl, thiophenyl, oxadiazolyl, thiadiazolyl, triazolyl, tetrazolyl, pyridinyl, pyrazinyl, pyrimidinyl, pyridazinyl or triazinyle groups;

by way of examples of a bicyclic heteroaryl, mention may be made of indolyl, isoindolyl, benzofuranyl, benzothiophenyl, benzoxazolyl, benzimidazolyl, indazolyl, benzothiazolyl, isobenzofuranyl, isobenzothiazolyl, pyrrolo[2,3-c]pyridinyl, pyrrolo[2,3-b]pyridinyl, pyrrolo[3,2-b]pyridinyl, pyrrolo[3,2-c]pyridinyl, quinolinyl, isoquinolinyl, cinnolinyl, quinazolinyl or quinoxalinyl groups;

by way of examples of a tricyclic heteroaryl, mention may be made of pyrido[1,2-a]benzimidazolyl, thiazolo[1,2-a]benzimidazolyl, imidazo[1,2-a]benzimidazolyl, pyrimido[1,2-a]benzimidazolyl or pyrazino[1,2-a]benzimidazolyl groups;

the term "a silanyl" is intended to mean: an —Si$(X_1)(X_2)(X_3)$ group where $X_1$, $X_2$ and $X_3$ are as defined in general formula (I);

the term "a halogen atom" is intended to mean: a fluorine, a chlorine, a bromine or an iodine;

"oxo" means "=O";

"thio" means "=S".

The compounds of formula (I) may comprise one or more asymmetrical carbon atoms. They may therefore exist in the form of enantiomers or of diastereoisomers. These enantiomers and diastereoisomers, and also mixtures thereof, including racemic mixtures, form part of the invention.

The compounds of formula (I) may exist in the form of bases or of addition salts with acids. Such addition salts form part of the invention.

These salts are advantageously prepared with pharmaceutically acceptable acids, but the salts of other acids that are useful, for example, for purifying or isolating the compounds of formula (I) also form part of the invention.

The compounds of general formula (I) may be in the form of hydrates or of solvates, i.e. in the form of associations or combinations with one or more molecules of water or with a solvent. Such hydrates and solvates also form part of the invention.

Among the compounds of general formula (I) which are subjects of the invention, a first subgroup of compounds is constituted by the compounds for which:

one of $G_1$, $G_2$, $G_3$ and $G_4$ is a C—X group where X is an —Si$(X_1)(X_2)(X_3)$ group; the others of $G_1$, $G_2$, $G_3$ and $G_4$ being a CH group;

$X_1$, $X_2$ and $X_3$ are, independently of one another, a $C_1$-$C_6$-alkyl, $C_3$-$C_7$-cycloalkyl or aryl group.

Among the compounds of general formula (I) which are subjects of the invention, a second subgroup of compounds is constituted by the compounds for which:

one of $G_1$, $G_2$, $G_3$ and $G_4$ is a C—X group where X is an —Si$(X_1)(X_2)(X_3)$ group; the others of $G_1$, $G_2$, $G_3$ and $G_4$ being a CH group;

$X_1$, $X_2$ and $X_3$ are, independently of one another, a methyl, ethyl, isopropyl, tert-butyl, cyclohexyl or phenyl group.

Among the compounds of general formula (I) which are subjects of the invention, a third subgroup of compounds is constituted by the compounds for which:

n is equal to 1.

Among the compounds of general formula (I) which are subjects of the invention, a fourth subgroup of compounds is constituted by the compounds for which:

Y is an aryl or a heteroaryl; the aryl or the heteroaryl being optionally substituted with one or more groups chosen from a halogen atom or a $C_1$-$C_6$-fluoroalkyl group.

Among the compounds of general formula (I) which are subjects of the invention, a fifth subgroup of compounds is constituted by the compounds for which:

Y is a phenyl or a pyridinyl; the phenyl being optionally substituted with one or more groups chosen from a fluorine atom or a $CF_3$ group.

Among the compounds of general formula (I) which are subjects of the invention, a sixth subgroup of compounds is constituted by the compounds for which:

$Z_1$, $Z_2$, $Z_3$ and $Z_4$ are, independently of one another, a nitrogen atom or a C($R_6$) group, one corresponding to a nitrogen atom and the others corresponding to a C($R_6$) group;

$R_6$ is a hydrogen atom.

Among the compounds of general formula (I) which are subjects of the invention, a seventh subgroup of compounds is constituted by the compounds for which:

$Z_4$ is a nitrogen atom and $Z_1$, $Z_2$ and $Z_3$ are a CH group.

Among the compounds of the general formula (I) which are subjects of the invention, an eighth subgroup of compounds is constituted by the compounds for which:

Z is a cyclic amine linked via the nitrogen atom, of formula:

in which:
- A is a $C_1$-$C_7$-alkylene group optionally substituted with one or two $R_8$ groups;
- B is a $C_1$-$C_7$-alkylene group optionally substituted with one or two $R_9$ groups;
- L is a bond, or a sulphur, oxygen or nitrogen atom; the nitrogen atom being optionally substituted with an $R_{10}$ or $R_{11}$ group;

the carbon atoms of the cyclic amine Z being optionally substituted with one or more $R_{12}$ groups which may be identical to or different from one another;

$R_8$, $R_9$, $R_{10}$, $R_{11}$ and $R_{12}$ being as defined in general formula (I).

Among the compounds of general formula (I) which are subjects of the invention, a ninth subgroup of compounds is substituted by the compounds for which:

Z is a cyclic amine linked via the nitrogen atom, of formula:
in which:

A is a $C_1$-$C_7$alkylene group;
B is a $C_1$-$C_7$alkylene group;
L is a bond, or a sulphur, oxygen or nitrogen atom; the nitrogen atom being optionally substituted with an $R_{11}$ group;

the carbon atoms of the cyclic amine Z being optionally substituted with one or more $R_{12}$ groups which may be identical to or different from one another;

$R_{11}$ and $R_{12}$ being as defined in general formula (I).

Among the compounds of general formula (I) which are subjects of the invention, a tenth subgroup of compounds is constituted by the compounds for which:

Z is a cyclic amine linked via the nitrogen atom, of formula:
in which:

A is a $C_1$-$C_7$alkylene group;
B is a $C_1$-$C_7$alkylene group;
L is a bond;

the carbon atoms of the cyclic amine Z being optionally substituted with one or more $R_{12}$ groups which may be identical to or different from one another;

$R_{12}$ being as defined in general formula (I).

Among the compounds of general formula (I) which are subjects of the invention, an eleventh subgroup of compounds is constituted by the compounds for which:

Z is a cyclic amine linked via the nitrogen atom, of formula:

in which:
- A is a $C_1$-$C_3$-alkylene group;
- B is a $C_1$-$C_3$-alkylene group;
- L is a bond;

the carbon atoms of the cyclic amine Z being optionally substituted with one or more $R_{12}$ groups which may be identical to or different from one another;

$R_{12}$ is a hydroxyl group.

Among the compounds of general formula (I) which are subjects of the invention, a twelfth subgroup of compounds is constituted by the compounds for which:

Z is an azetidinyl or pyrrolidinyl group;

the carbon atoms of the cyclic amine Z being optionally substituted with one or more $R_{12}$ groups which may be identical to or different from one another;

$R_{12}$ is a hydroxyl group.

Among the compounds of general formula (I) which are subjects of the invention, a thirteenth subgroup of compounds is constituted by the compounds for which:

Z is an acyclic amine, linked via the nitrogen atom, of formula NRaRb in which Ra and Rb are, independently of one another, a hydrogen atom or a $C_1$-$C_6$-alkyl group.

Among the compounds of general formula (I) which are subjects of the invention, a fourteenth subgroup of compounds is constituted by the compounds for which:

Z is an acyclic amine, linked via the nitrogen atom, of formula NRaRb in which Ra and Rb are, independently of one another, a $C_1$-$C_6$-alkyl group, more particularly methyl.

Among the compounds of general formula (I) which are subjects of the invention, a fifteenth subgroup of compounds is constituted by the compounds for which the definitions of $G_1$, $G_2$, $G_3$ and $G_4$, n, Y, $Z_1$, $Z_2$, $Z_3$, $Z_4$ and Z given above are combined.

Among the compounds of general formula (I) which are subjects of the invention, a sixteenth subgroup of compounds is constituted by the compounds for which:

one of $G_1$, $G_2$, $G_3$ and $G_4$ is a C—X group where X is an —Si($X_1$)($X_2$)($X_3$) group; the others of $G_1$, $G_2$, $G_3$ and $G_4$ being a CH group;

$X_1$, $X_2$ and $X_3$ are, independently of one another, a $C_1$-$C_6$-alkyl, $C_3$-$C_7$-cycloalkyl or aryl group;

n is equal to 1;

Y is an aryl or a heteroaryl; the aryl or the heteroaryl being optionally substituted with one or more groups chosen from a halogen atom or a $C_1$-$C_6$-fluoroalkyl group;

$Z_1$, $Z_2$, $Z_3$ and $Z_4$ are, independently of one another, a nitrogen atom or a $C(R_6)$ group, one corresponding to a nitrogen atom and the others corresponding to a $C(R_6)$ group;

$R_6$ is a hydrogen atom;

Z is:

either a cyclic amine linked via the nitrogen atom, of formula:

in which:

A is a $C_1$-$C_3$-alkylene group;

B is a $C_1$-$C_3$-alkylene group;

L is a bond;

the carbon atoms of the cyclic amine Z being optionally substituted with one or more $R_{12}$ groups which may be identical to or different from one another;

$R_{12}$ is a hydroxyl group;

or an acyclic amine, linked via the nitrogen atom, of formula NRaRb in which Ra and Rb are, independently of one another, a hydrogen atom or a $C_1$-$C_6$-alkyl group.

Among the compounds of general formula (I) which are subjects of the invention, mention may in particular be made of the following compounds:

1. N-[6-(azetidin-1-yl)pyridin-3-yl]-6-trimethylsilyl-1-[(3-fluorophenyl)methyl]-1H-indole-2-carboxamide
2. N-[6-(3-hydroxyazetidin-1-yl)pyridin-3-yl]-6-trimethylsilyl-1-[(3-fluorophenyl)methyl]-1H-indole-2-carboxamide
3. N-[6-(azetidin-1-yl)pyridin-3-yl]-5-trimethylsilyl-1-[(3-fluorophenyl)methyl]-1H-indole-2-carboxamide
4. N-[6-(3-hydroxyazetidin-1-yl)pyridin-3-yl]-5-trimethylsilyl-1-[(3-fluorophenyl)methyl]-1H-indole-2-carboxamide
5. N-[6-(azetidin-1-yl)pyridin-3-yl]-7-trimethylsilyl-1-[(3-fluorophenyl)methyl]-1H-indole-2-carboxamide
6. N-[6-(3-hydroxyazetidin-1-yl)pyridin-3-yl]-7-trimethylsilyl-1-[(3-fluorophenyl)methyl]-1H-indole-2-carboxamide
7. N-[6-(Dimethylamino)pyridin-3-yl]-5-trimethylsilyl-1-[(3-fluorophenyl)methyl]-1H-indole-2-carboxamide
8. N-[6-(azetidin-1-yl)pyridin-3-yl]-5-(ethyl)dimethylsilyl-1-[(3-fluorophenyl)methyl]-1H-indole-2-carboxamide
9. N-[6-(azetidin-1-yl)pyridin-3-yl]-5-(cyclohexyl)dimethylsilyl-1-[(3-fluorophenyl)methyl]-1H-indole-2-carboxamide
10. N-[6-(azetidin-1-yl)pyridin-3-yl]-6-trimethylsilyl-1-[[(3-trifluoromethyl)phenyl]methyl]-1H-indole-2-carboxamide
11. N-[6-(3-hydroxyazetidin-1-yl)pyridin-3-yl]-6-trimethylsilyl-1-[[(3-trifluoromethyl)phenyl]methyl]-1H-indole-2-carboxamide
12. N-[6-(azetidin-1-yl)pyridin-3-yl]-5-(diphenyl)methylsilyl-1-[(3-fluorophenyl)methyl]-1H-indole-2-carboxamide
13. N-[6-(azetidin-1-yl)pyridin-3-yl]-5-trimethylsilyl-1-[[(3-trifluoromethyl)phenyl]methyl]-1H-indole-2-carboxamide
14. N-[6-(3-hydroxyazetidin-1-yl)pyridin-3-yl]-5-trimethylsilyl-1-[[(3-trifluoromethyl)phenyl]methyl]-1H-indole-2-carboxamide
15. N-[6-(3-hydroxyazetidin-1-yl)pyridin-3-yl]-6-trimethylsilyl-1-[(pyridin-4-yl)methyl]-1H-indole-2-carboxamide
16. N-[6-(azetidin-1-yl)pyridin-3-yl]pyridin-3-yl]-6-trimethylsilyl-1-[(pyridin-4-yl)methyl]-1H-indole-2-carboxamide
17. N-[6-(azetidin-1-yl)pyridin-3-yl]-5-triethylsilyl-1-[(3-fluorophenyl)methyl]-1H-indole-2-carboxamide
18. N-[6-(azetidin-1-yl)pyridin-3-yl]-5-tert-butyl(dimethyl)silyl-1-[(3-fluorophenyl)methyl]-1H-indole-2-carboxamide
19. N-[6-(Pyrrolidin-1-yl)pyridin-3-yl]-5-(cyclohexyl)dimethylsilyl-1-[(3-fluorophenyl)methyl]-1H-indole-2-carboxamide
20. N-[6-(azetidin-1-yl)pyridin-3-yl]-5-phenyldimethylsilyl-1-[(3-fluorophenyl)methyl]-1H-indole-2-carboxamide
21. N-[6-(azetidin-1-yl)pyridin-3-yl]-5-(isopropyl)dimethylsilyl-1-[(3-fluorophenyl)methyl]-1H-indole-2-carboxamide
22. N-[6-(Azetidin-1-yl)pyridin-3-yl]-5-(methyl)diethylsilyl-1-[(3-fluorophenyl)methyl]-1H-indole-2-carboxamide.

Among the compounds of general formula (I) which are subjects of the invention, a seventeenth subgroup of compounds is constituted by the compounds for which:

$G_1$, $G_2$, $G_3$ and $G_4$ are, independently of one another, a C—X group;

X is chosen from a hydrogen atom or an —Si($X_1$)($X_2$)($X_3$) group; one of $G_1$, $G_2$, $G_3$ and $G_4$ and at most one of $G_1$, $G_2$, $G_3$ and $G_4$ is a C—X group where X is an —Si($X_1$)($X_2$)($X_3$) group;

$X_1$, $X_2$ and $X_3$ are, independently of one another, a $C_1$-$C_6$-alkyl group.

Among the compounds of general formula (I) which are subjects of the invention, an eighteenth subgroup of compounds is constituted by the compounds for which n is equal to 1 and Y is an aryl, more particularly a phenyl, optionally substituted with one or more halogen atoms, more particularly fluorine atoms.

Among the compounds of general formula (I) which are subjects of the invention, a nineteenth subgroup of compounds is constituted by the compounds for which $Z_1$, $Z_2$, $Z_3$ and $Z_4$ are, independently of one another, a nitrogen atom or a $C(R_6)$ group, one corresponding to a nitrogen atom and the others corresponding to a $C(R_6)$ group;

where $R_6$ is a hydrogen atom.

Among the compounds of general formula (I) which are subjects of the invention, a twentieth subgroup of compounds is constituted by the compounds for which:

Z is a cyclic amine linked via the nitrogen atom, of formula:

in which:

A is a $C_1$-$C_7$ alkylene group optionally substituted with one or two $R_8$ groups;

B is a $C_1$-$C_7$alkylene group optionally substituted with one or two $R_9$ groups;

L is a bond, or a sulphur, oxygen or nitrogen atom; the nitrogen atom being optionally substituted with an $R_{10}$ or $R_{11}$ group;

the carbon atoms of the cyclic amine Z being optionally substituted with one or more $R_{12}$ groups which may be identical to or different from one another.

Among the compounds of general formula (I) which are subjects of the invention, a twenty-first subgroup of compounds is constituted by the compounds for which:

Z is a cyclic amine linked via the nitrogen atom, of formula:

this cyclic amine being an azetidinyl group;
the carbon atoms of the cyclic amine Z being optionally substituted with an $R_{12}$ group;
$R_{12}$ is a hydroxyl group.

Among the compounds of general formula (I) which are subjects of the invention, a twenty-second subgroup of compounds is constituted by the compounds for which:

$G_1$, $G_2$, $G_3$ and $G_4$ are, independently of one another, a C—X group;

X is chosen from a hydrogen atom or an —Si($X_1$)($X_2$)($X_3$) group;

one of $G_1$, $G_2$, $G_3$ and $G_4$ and at most one of $G_1$, $G_2$, $G_3$ and $G_4$ is a C—X group where X is an —Si($X_1$)($X_2$)($X_3$) group;

$X_1$, $X_2$ and $X_3$ are, independently of one another, a $C_1$-$C_6$-alkyl group;

n is equal to 1;

Y is an aryl, more particularly a phenyl, optionally substituted with one or more halogen atoms, more particularly fluorine atoms;

$Z_1$, $Z_2$, $Z_3$ and $Z_4$ are, independently of one another, a hydrogen atom or a C($R_6$) group, one corresponding to a nitrogen atom and the others corresponding to a C($R_6$) group;

where $R_6$ is a hydrogen atom;

Z is a cyclic amine linked via the nitrogen atom, of formula:

this cyclic amine being an azetidinyl group;
the carbon atoms of the cyclic amine Z being optionally substituted with an $R_{12}$ group;
where $R_{12}$ is a hydroxyl group.

In the subsequent text, the term "leaving group" is intended to mean a group that can be readily cleaved from a molecule by heterolytic bond breaking, with the departure of a pair of electrons. This group can thus be readily replaced with another group in a substitution reaction, for example. Such leaving groups are, for example, halogens or an activated hydroxyl group such as a methanesulphonate, benzenesulphonate, p-toluenesulphonate, triflate, acetate, etc. Examples of leaving groups and also references for the preparation thereof are given in "Advances in Organic Chemistry", J. March, 5$^{th}$ Edition, Wiley Interscience, 2001.

In accordance with the invention, the compounds of general formula (I) can be prepared according to the process illustrated by scheme 1 which follows.

According to scheme 1, the compounds of general formula (IV) can be obtained by reacting a compound of general formula (II), in which $G_1$, $G_2$, $G_3$ and $G_4$ are as defined in general formula (I) and B is a $C_1$-$C_6$-alkoxyl group, with a compound of general formula (III), in which Y and n are as defined in general formula (I) and LG is a leaving group or LG is a hydroxyl group.

In scheme 1, when the compound of general formula (III) is defined such that n is equal to 1, 2 or 3 and LG is a leaving group such as a chlorine, bromine or iodine atom, the reaction for formation of the compounds of general formula (IV) can be carried out in the presence of a base such as sodium hydride or potassium carbonate, in a polar solvent such as dimethylformamide, dimethyl sulphoxide or acetone (n=1: Kolasa T., *Bioorg. Med. Chem.* 1997, 5 (3) 507, n=2: Abramovitch R., *Synth. Commun.*, 1995, 25 (1), 1).

When the compound of general formula (III) is defined such that n is equal to 1, 2 or 3 and LG is a hydroxyl group, the compounds of general formula (IV) can be obtained by reacting the compound of general formula (II) with a compound of general formula (III) in the presence of a phosphine such as, for example, triphenylphosphine, and a reactant such as, for example, diethyl azodicarboxylate in solution in a solvent such as dichloromethane or tetrahydrofuran (O. Mitsonobu, *Synthesis*, 1981, 1-28).

Scheme 1

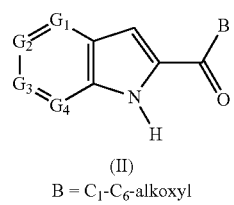

(II)
B = $C_1$-$C_6$-alkoxyl

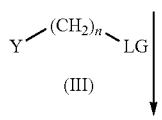

(III)

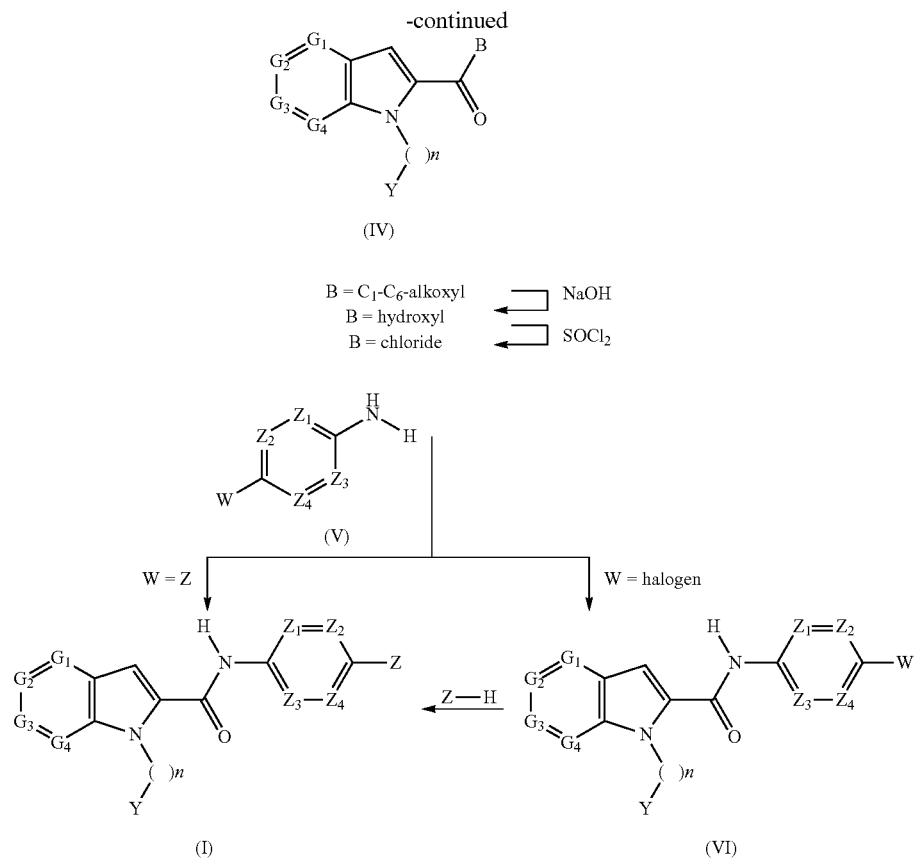

Similarly, the compounds of general formula (IV) can be obtained by reacting the compound of general formula (II) with a compound of general formula (III), in the presence of a phosphine supported on a resin, and a reactant such as, for example, diisopropyl azodicarboxylate in solution in a solvent such as dichloromethane or tetrahydrofuran.

When the compound of general formula (III) is defined such that n is equal to 0 and LG is a leaving group such as a chlorine, bromine or iodine atom, the reaction for formation of compounds of general formula (IV) can be carried out by application and adaptation of the methods described by S. L. Buchwald et al. (*J. Am. Chem. Soc.*, 2001, 123, 7727 and 2002, 124, 11684), preferably under an inert atmosphere in a basic medium, for example in the presence of potassium triphosphate, in the presence of a copper salt such as copper iodide, optionally in the presence of an additive such as N,N'-dimethylcyclohexane-1,2-diamine, the whole in an organic solvent such as toluene.

The compound of general formula (IV), for which B is a $C_1$-$C_6$-alkoxyl group, can be converted to a compound of general formula (IV), where B is a hydroxyl group, by the action of a base such as sodium hydroxide or potassium hydroxide in solution in a solvent such as ethanol. The compound of general formula (IV), where B is a hydroxyl group, can subsequently be converted to a compound of general formula (IV), where B is a chlorine atom, by the action of a chlorinating agent such as thionyl chloride in a solvent such as dichloromethane.

The compound of general formula (VI) can subsequently be obtained, for example, by reacting a compound of general formula (IV), where B is a chlorine atom, as obtained above, with an amine of general formula (V), in which $Z_1$, $Z_2$, $Z_3$ and $Z_4$ are as defined in general formula (I) and W is a halogen such as a chlorine atom, in a solvent such as dichloroethane, toluene or tetrahydrofuran.

The compound of general formula (VI) can also be obtained by reacting a compound of general formula (IV), where B is a hydroxyl group, as obtained above, with an amine of general formula (V), in which $Z_1$, $Z_2$, $Z_3$ and $Z_4$ are as defined in general formula (I) and W is a halogen atom such as a chlorine atom, in the presence of a coupling agent such as diethyl cyanophosphonate or N-(3-dimethylaminopropyl)-N'-ethylcarbodiimide, optionally in the presence of a base such as triethylamine, in a solvent such as dimethylformamide.

The compound of general formula (I) can be obtained, for example, by reacting a compound of general formula (IV), where B is a chlorine atom, as obtained above, with an amine of general formula (V), in which W=Z and Z, $Z_1$, $Z_2$, $Z_3$ and $Z_4$ are as defined in general formula (I), in a solvent such as dichloroethane, toluene or tetrahydrofuran.

The compound of general formula (I) can also be obtained by reacting a compound of general formula (IV), where B is a hydroxyl group, as obtained above, with an amine of general formula (V), in which W=Z and Z, $Z_1$, $Z_2$, $Z_3$ and $Z_4$ are as defined in general formula (I), in the presence of a coupling agent such as diethyl cyanophosphonate or N-(3-dimethylaminopropyl)-N'-ethylcarbodiimide, and optionally in the presence of a base such as triethylamine, in a solvent such as dimethylformamide.

The compound of general formula (I) can also be obtained by reacting a compound of general formula (VI) in the presence of an amine of formula Z-H, in which Z is as defined in general formula (I), without solvent or in a solvent such as N-methylpyrrolidone, or else by application and adaptation of the methods described by S. L. Buchwald et al. (*J. Am. Chem. Soc.*, 2001, 123, 7727 and 2002, 124, 11684), preferably under an inert atmosphere in a basic medium, for example in the presence of potassium triphosphate, in the presence of a copper salt such as copper iodide, optionally in the presence of an additive such as N,N'-dimethylcyclohexane-1,2-diamine, the whole in an organic solvent such as toluene, or else by application and adaptation of the methods described by Hartwig et al. (*Angewandte Chemie*, 2005, 44, 1371-1375), for example in the presence of a base and of catalytic amounts of a palladium-based catalyst, such as palladium diacetate, and of a phosphine.

The compounds of general formula (II) of scheme 1, in which $G_1$, $G_2$, $G_3$ and $G_4$ are as defined in general formula (I) and B is a $C_1$-$C_6$-alkoxyl group, can, when their method of preparation is not described, be obtained, for example, according to the method illustrated in scheme 2.

Scheme 2

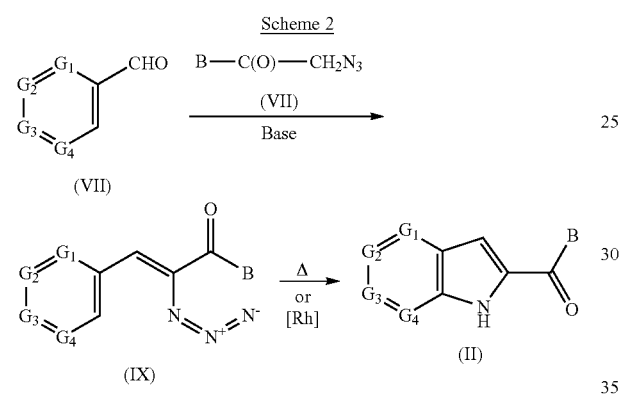

The compounds of general formula (II) are prepared starting from aromatic or heteroaromatic aldehydes substituted with a silanyl group of general formula (VII) in which $G_1$, $G_2$, $G_3$ and $G_4$ are as defined in general formula (I), by reaction with an alkyl azidoacetate of general formula (VIII) in which B is a $C_1$-$C_6$-alkoxyl group, such as ethyl azidoacetate for example, in the presence of a base such as sodium ethoxide, in a solvent such as ethanol or methanol, so as to give the alkyl azido-2-cinnamates of general formula (IX). The latter are subsequently converted to indole or azaindole esters at the reflux of a solvent, for example in xylene or toluene, by adaptation of protocols described in the literature (Hemetsberger et al *Monatsh. Chem.*, 1969, 100, 1599 and 1970, 101, 161; P. Roy et al *Synthesis.*, 2005, 16, 2751-2757; R. Guilard et al *J. Heterocyclic. Chem.*, 1981, 18, 1365-1377; W. Rees et al *J. Chem. Soc, perkin trans* 1 1984, 2189-2196; P. Molina et al *J. org. Chem.*, 2003, 68(2), 489-499; C. Moody et al *J. Chem. Soc., Perkin Trans.* 1 1984, 2189-2196; J. Sawyer et al *J. Med. Chem.*, 2005, 48, 893-896; D. Tanner *Synlett* 2006, 18, 3140-3144).

Alternatively, according to scheme 2, the formation of the compounds of general formula (II) can be obtained by decomposition of the alkyl azido-2-cinnamate of general formula (IX), in the presence of a rhodium dimer complex, in a solvent such as toluene at a temperature of between 25° C. and 60° C., according to an adaptation of protocols described in the literature (Tom G. Drivers et al *J. Am. Chem. Soc.*, 2007, 129, 7500-7501; J. Sawyer et al *J. Med. Chem.*, 2005, 48, 893-896).

The silanyl group of the compounds of general formula (II) can also be introduced by reacting the corresponding indole or azaindole ester substituted with a halogen, such as a bromine or an iodine, in the position where the silanyl group should be introduced, in the presence of a disilane, such as hexamethyldisilane, of a catalytic amount of a metal complex, preferably a palladium complex, for example tetrakis (triphenylphosphine)palladium, and of a base, in a solvent such as toluene, at a temperature of between 20° C. and the boiling point of the solvent.

The silanyl group of the compounds of the general formula (II) can also be introduced by reacting the corresponding indole or azaindole ester substituted with a halogen, such as an iodine, in the position where the silanyl group should be introduced, in the presence of a silane, such as triethylsilane, of a catalytic amount of a metal complex, preferably a palladium complex, for instance bis(tri-tert-butylphosphine)palladium, and of a base such as potassium triphosphate, in a solvent such as N-methyl-2-pyrrolidinone, at a temperature close to 20° C. (adaptation of the protocols described in the literature: Yoshinori Yamanoi et al *J. org. Chem.*, 2005, 70 (23), 9607-9609 and cited references).

The aromatic or heteroaromatic aldehydes substituted with a silanyl group of general formula (VII) can, when they are not commercially available, be obtained starting from the corresponding aromatic or heteroaromatic aldehydes, preferably masked in the form of an acetal, for example, substituted with a halogen atom, such as a bromine or an iodine, in the position where the silanyl group should be introduced:

for example by reaction with a disilane such as hexamethyldisilane, in the presence of a catalytic amount of a metal complex, preferably a palladium complex, for instance tetrakis(triphenylphosphine)palladium, without solvent or in a solvent, preferably a polar solvent, for instance hexamethylphosphoramide, in the presence of a base such as potassium carbonate, at a temperature of between 20° C. and the boiling point of the solvent (adaptation of the protocols described in the literature: J. Babin et al *J. organometal. Chem.*, 1993, 446 (1-2), 135-138; E. Shirakawa et al *Chem. Commun.*, 2000, 1895-1896; L. Goossen et al *Synlett*, 2000, 1801-1803; H. Matsumoto et al *J. organometal. Chem.*, 1975, 85, C1; FR2677358);

for example by reaction with a disilane such as hexamethyldisilane, in the presence of a strong base, for instance potassium methoxide or sodium methoxide, in a polar solvent, for instance hexamethylphosphoric triamide (HMPT), at a temperature close to 20° C. (adaptation of the protocols described in the literature: A. I Meyers et al *J. org. Chem.*, 1977, 42 (15), 2654-2655; K. Ishimaru et al *Heterocycles.*, 2001, 55 (8), 1591-1597);

for example by reaction with a silane such as triethylsilane, in the presence of a catalytic amount of a metal complex, preferably a palladium complex, for instance bis(tri-tert-butylphosphine)palladium, and of a base such as potassium triphosphate, in a solvent such as N-methyl-2-pyrrolidinone, at a temperature close to 20° C. (adaptation of the protocols described in the literature: Yoshinori Yamanoi et al *J. org. Chem.*, 2005, 70 (23), 9607-9609 and cited references).

The aromatic or heteroaromatic aldehydes substituted with a silanyl group of general formula (VII) according to scheme 2 can, when they are not commercially available, also be obtained starting from the corresponding dihalogenated aromatics or heteroaromatics, such as a derivative which is dibrominated, in the position where the silanyl group should be introduced, by exchange with an organometallic compound, for instance n-butyllithium. The metal aromatics or heteroaromatics thus formed can subsequently react with organohalosilanes or be converted to formylated derivatives by adaptation of the methods described in the literature. The reaction is preferably carried out at low temperatures of between −110° C. and ambient temperature, in a solvent such as ether or THF (adaptation of the protocols described in the literature: Bao-Hui Ye et al *Tetrahedron.*, 2003, 59, 3593-3601; P. Pierrat et al *Synlett* 2004, 13, 2319-2322; K. T. Warner et al *Heterocycles* 2002, 58, 383; D. Deffieux et al *J. organometal. Chem.*, 1994, 13 (6), 2415-2422; WO2005080328; S. G. Davies et al *J. Chem. Soc, perkin trans* 1 1991, 501; G. Queguiner et al *J. Org. Chem.*, 1981, 46, 4494-4497; G. Breton et al. *Tetrahedron* 2000, 56 (10), 1349-1360; S. De Montis et al. *Tetrahedron* 2004, 60 (17), 3915-3920; L. Buchwald et al *J. Am. Chem. Soc.*, 1998, 120, 4960-4976).

According to scheme 3, the silanyl group of $G_1$, $G_2$, $G_3$ or $G_4$ of the compounds of general formula (I) can also be introduced by starting from the compounds of general formula (X), in which $A_1$, $A_2$, $A_3$ and $A_4$ are, independently of one another, a C—X group or a nitrogen atom; X being as defined in general formula (I); one of $A_1$, $A_2$, $A_3$ and $A_4$ and at most one of $A_1$, $A_2$, $A_3$ and $A_4$ is a C-q group where q is a halogen atom, such as an iodine or a bromine, in the position where the silanyl group should be introduced. For example, the reaction can be carried out in the presence of a silane, such as triethylsilane, of a catalytic amount of a metal complex, preferably a palladium complex, for instance bis(tri-tert-butylphosphine)palladium, and of a base such as potassium triphosphate, preferably under an inert atmosphere, in a solvent such as N-methyl-2-pyrrolidinone, at a temperature close to 20° C., or else by application and adaptation of the methods described by Yoshinori Yamanoi et al. *J. org. Chem.*, 2005, 70 (23), 9607-9609 and cited references.

Scheme 3

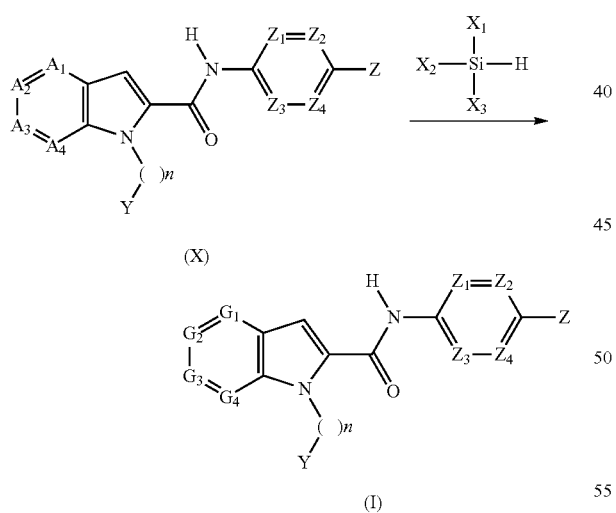

(X)

(I)

The compounds of general formula (X) as defined above can be obtained, for example, by analogy with the preparation of the compounds of general formula (I) described above or by adaptation of the protocols described in the literature (WO2007010138) and known to those skilled in the art.

The compounds of general formula (I), in which Z is an acyclic amine NRaRb corresponding to an $NH_2$ group, can be obtained, according to conditions known to those skilled in the art and described in the literature (Greene, Wuts, *Protective groups in organic synthesis*, Wiley-Interscience), from precursors of general formula (I) where NRaRb=NH-GP, GP corresponding to a protective group such as an acetyl or tert-butoxycarbonyl group.

The compounds of general formula (I) comprising a $CO_2H$ group can be obtained, according to conditions known to those skilled in the art and described in the literature (Greene, Wuts, *Protective groups in organic synthesis*, Wiley-Interscience), from precursors of general formula (I) comprising a $CO_2GP$ group, GP corresponding to a carboxylic acid-protecting group, such as a methyl or tert-butyl group.

The compounds of general formula (I) comprising a $CH_2OH$ group can be obtained, according to conditions known to those skilled in the art, from compounds of general formula (I) comprising a $CO_2$alkyl group, for example, by reaction in the presence of a reducing agent such as sodium borohydride in a solvent such as tetrahydrofuran.

The compounds of general formula (III) are commercially available, described in the literature (Carling R. W. et al *J. Med. Chem.* 2004 (47), 1807-1822 or Russel M. G. N. et al. *J. Med. Chem.* 2005 (48), 1367-1383) or accessible using methods known to those skilled in the art.

The compounds of general formula (V) and the other reactants, when the method for preparing them is not described, are commercially available or described in the literature (WO2005028452, WO2002048152, WO2006040522, WO2004052869, WO2004062665, WO2005035526, WO2004110986, *Heterocycles* 1977, 6(12), 1999-2004, for example).

According to another of its aspects, a subject of the invention is also the compounds of general formulae (IVa), (IVb), (IVc), (IVd), (IVe) and (IVf). These compounds are of use as intermediates for the synthesis of the compounds of formula (I).

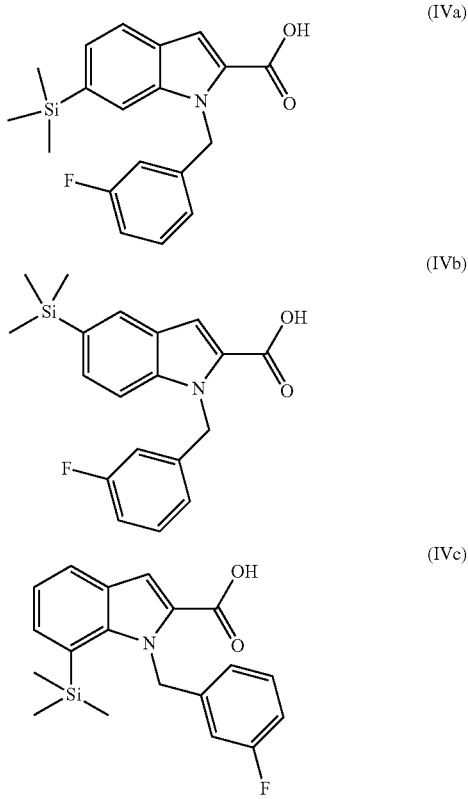

-continued

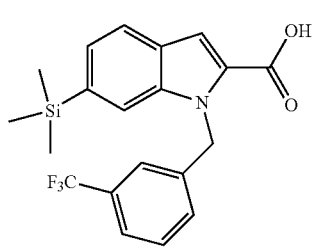
(IVd)

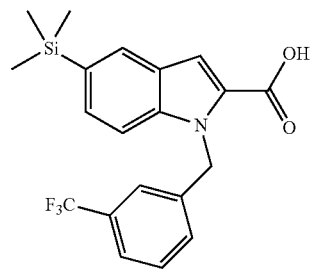
(IVe)

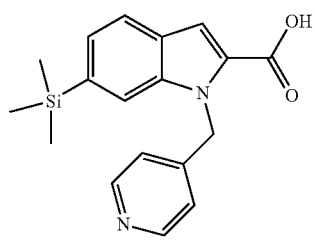
(IVf)

The acids (IVa), (IVb), (IVc), (IVd), (IVe) and (IVf) are prepared according to the processes described in examples No. 1, 3, 5, 10, 13 and 15.

The following examples describe the preparation of a number of compounds in accordance with the invention. These examples are not limiting and merely illustrate the present invention. The numbers of the compounds exemplified refer back to those given in table 1. The elemental microanalyses, the LC-MS (liquid chromatography-mass spectroscopy) analyses, the IR spectra or the NMR spectra confirm the structures of the compounds obtained.

EXAMPLE 1

Compound No. 1

N-[6-(azetidin-1-yl)pyridin-3-yl]-6-trimethylsilyl-1-[(3-fluorophenyl)methyl]-1H-indole-2-carboxamide 1.1. Ethyl 2-azido-3-(4-trimethylsilylphenyl)propenoate 1.26 g (54.96 mmol) of sodium and 30 ml of anhydrous ethanol are introduced into a 100 ml round-bottomed flask equipped with a magnetic stirrer and maintained under a nitrogen atmosphere. The reaction mixture is stirred at ambient temperature until a homogeneous solution is obtained. A solution containing 16.83 ml (54.96 mmol) of ethyl azidoacetate (34% in $CH_2Cl_2$) and 5 g (27.48 mmol) of 4-trimethylsilylbenzaldehyde in 5 ml of ethanol is added dropwise to this solution, cooled to −10° C. The reaction mixture is subsequently stirred at 0° C. for 4 hours. The reaction medium is hydrolysed by adding 100 ml of an ammonium chloride solution (30% aqueous) with vigorous stirring. The product is extracted with three times 50 ml of ethyl acetate. The combined organic phases are washed with twice 20 ml of water, dried over sodium sulphate and concentrated under reduced pressure. The resulting oil is purified by silica gel column chromatography, elution being carried out with a mixture of heptane and dichloromethane. 4.96 g of the expected product are isolated in the form of a yellow oil.

$^1$H NMR (DMSO $D_6$), δ (ppm): 7.6 (d, 2H); 7.35 (d, 2H); 6.7 (s, 1H); 4.1 (q, 2H); 1.1 (t, 3H); 0 (s, 9H).

1.2 Ethyl 6-trimethylsilyl-1H-indole-2-carboxylate 0.17 g (0.16 mmol) of the dirhodium heptafluorobutyrate dimer complex is added to a solution of 1.0 g (3.14 mmol) of ethyl 2-azido-3-(4-trimethylsilylphenyl)propenoate obtained in stage 1.1, in 20 ml of dry toluene, maintained under an inert atmosphere. The reaction mixture is then stirred for 12 h at 70° C. After a return to ambient temperature, the reaction mixture is filtered through silica gel, elution being carried out with ethyl acetate. The filtrate is subsequently concentrated under reduced pressure. The residue is purified by silica gel column chromatography, elution being carried out with a mixture of heptane and dichloromethane. 0.61 g of the expected product is isolated in the form of a beige powder.

Mp=127-129° C.

$^1$H NMR (DMSO $D_6$), δ (ppm): 11.7 (s, 1H); 7.41 (dd, 1H); 7.39 (d, 1H); 6.97 (dd, 1H); 6.88 (d, 1H); 4.1 (q, 2H); 1.1 (t, 3H); 0.0 (s, 9H).

1.3. Ethyl 6-trimethylsilyl-1-[(3-fluorophenyl)methyl]-1H-indole-2-carboxylate

A solution of 0.9 g (3.44 mmol) of ethyl 6-trimethylsilyl-1H-indole-2-carboxylate, obtained according to the protocol described in stage 1.2, in 5 ml of dry DMF is added dropwise to a suspension of 0.15 g (3.79 mmol) of sodium hydride (60%) in 5 ml of dry DMF, maintained under an inert atmosphere. The reaction mixture is stirred at ambient temperature for 2 hours. 0.82 g (4.13 mmol) of 3-fluorobenzyl bromide is subsequently added, dropwise, at ambient temperature. The reaction mixture is then stirred for 20 h at ambient temperature and then diluted with 100 ml of a mixture of water and ether (1/1). The resulting mixture is separated by settling out and the aqueous phase is extracted with 30 ml of ether. The combined organic phases are washed three times with water, dried over sodium sulphate, filtered and concentrated under reduced pressure. The resulting oil is purified by silica gel column chromatography, elution being carried out with a mixture of heptane and ethyl acetate. 0.89 g of the expected product is isolated.

Mp=87-88° C.

$^1$H NMR (DMSO $D_6$), δ (ppm): 7.65 (m, 1H); 7.35 (s, 1H); 7.32-7.1 (m, 3H); 6.9-6.6 (m, 3H); 5.80 (s, 2H); 4.25 (q, 2H); 1.3 (t, 3H); 0.2 (s, 9H).

1.4 6-Trimethylsilyl-1-[(3-fluorophenyl)methyl]-1H-indole-2-carboxylic acid (Compound No. IVa)

A solution of 0.85 g (2.30 mmol) of ethyl 5-trimethylsilyl-1-[(3-fluorophenyl)methyl]-1H-indole-2-carboxylate, obtained in stage 1.3, in 15 ml of ethanol and 5 ml of 1N sodium hydroxide is stirred at reflux for 4 hours. After this period of time, the reaction mixture is concentrated under reduced pressure and then taken up in 50 ml of water. The medium is acidified at pH 1 by successive additions of 1N hydrochloric acid. The precipitate is recovered by filtration, washed with water, and then dried under reduced pressure.

0.65 g of the expected product is thus isolated, which product is used as it is in the subsequent stage.

Mp=189-191° C.

$^1$H NMR (DMSO D$_6$), δ (ppm): 13.1 (broad peak, 1H); 7.7 (m, 2H); 7.3 (m, 3H); 7.1 (m, 1H); 6.9 (m, 2H); 5.9 (s, 2H); 0.35 (s, 9H).

1.5 2-(Azetidin-1-yl)-5-nitropyridine 4.7 g (80.76 mmol) of azetidine are added dropwise to a suspension, stirred at 20° C., of 27.9 g (0.201 mol) of potassium carbonate and of 11 g (67.3 mmol) of 2-chloro-5-nitropyridine in 100 ml of dimethylformamide. The mixture is stirred for 5 minutes at 20° C. and then for 6 hours at 70° C. After this period of time, the suspension is poured into a mixture of 300 ml of water and 300 ml of ethyl acetate. The aqueous phase is separated and then extracted with 200 ml of ethyl acetate. The organic phases are combined, washed three times with 250 ml of water and then dried over sodium sulphate and concentrated under reduced pressure. 11.7 g of the expected product are thus obtained in the form of a solid.

Mp=132-134° C.

$^1$H NMR (CDCl$_3$), δ (ppm): 8.92 (d, 1H); 8.09 (dxd, 1H); 6.07 (d, 1H); 4.12 (m, 4H); 2.46 (quint., 2H).

1.6 3-Amino-6-(azetidin-1-yl)pyridine

A suspension of 11.5 g (64.18 mmol) of 2-(azetidin-1-yl)-5-nitropyridine, prepared in the previous stage, and of 1 g of Pd/C at 10% in 400 ml of ethanol is stirred vigorously at 20° C. under 5 atmospheres of hydrogen for 4 hours. After this period of time, the mixture is filtered through a celite buffer and then concentrated under reduced pressure. 9.3 g of the expected product are thus obtained, which product is used as it is in the subsequent synthesis.

$^1$H NMR (DMSO D$_6$), δ (ppm): 7.57 (d, 1H); 6.92 (dxd, 1H); 6.2 (d, 1H); 4.46 (broad peak, 2H); 3.78 (m, 4H); 2.25 (quint., 2H).

1.7 N-[6-(Azetidin-1-yl)pyridin-3-yl]-6-trimethylsilyl-1-[(3-fluorophenyl)methyl]-1H-indole-2-carboxamide (Compound No. 1)

114 mg (0.59 mmol) of N-(3-dimethylaminopropyl)-N'-ethylcarbodiimide hydrochloride (EDAC) and 81 mg (0.59 mmol) of 1-hydroxybenzotriazole (HOBT) are added to a solution, stirred at 20° C. under an inert atmosphere, of 0.2 g (0.59 mmol) of 6-trimethyl-silyl-1-[(3-fluorophenyl)methyl]-1H-indole-2-carboxylic acid, prepared in stage 1.4, in 5 ml of DMF. The reaction mixture is stirred at ambient temperature for 15 minutes. 131 mg (0.88 mmol) of 3-amino-6-(azetidin-1-yl)pyridine, prepared in stage 1.6, are subsequently added to the reaction mixture. After stirring for 16 hours at 20° C., the reaction mixture is poured into a mixture of 30 ml of a saturated aqueous solution of NaHCO$_3$ and 30 ml of ethyl acetate. The resulting mixture is separated by settling out and the aqueous phase is extracted with 20 ml of ethyl acetate. The combined organic phases are washed three times with 30 ml of water, dried over sodium sulphate and then concentrated under reduced pressure. The product obtained is purified by silica column chromatography, elution being carried out with a mixture of dichloromethane and methanol. The solid obtained after evaporation of the solvent under reduced pressure is washed with isopropyl ether at reflux, filtered under hot conditions and then dried under reduced pressure. 170 mg of the expected product are thus isolated.

Mp=208-210° C.

$^1$H NMR (DMSO D$_6$), δ (ppm): 10.2 (s, 1H); 8.28 (d, 1H); 7.75 (dd, 1H); 7.6 (d, 1H); 7.58 (s, 1H); 7.2 (m, 3H); 7.0-6.8 (m, 3H); 6.3 (d, 1H); 5.8 (s, 2H); 3.8 (t, 4H); 2.2 (m, 2H); 0.15 (s, 9H).

EXAMPLE 2

Compound No. 2

N-[6-(3-Hydroxyazetidin-1-yl)pyridin-3-yl]-6-trimethylsilyl-1-[(3-fluorophenyl)methyl]-1H-indole-2-carboxamide 2.1 2-(3-Hydroxyazetidin-1-yl)-5-nitropyridine A mixture of 0.311 g (2.84 mmol) of 3-hydroxyazetidine hydrochloride, 0.3 g (1.89 mmol) of 2-chloro-5-nitropyridine and 0.41 ml (2.84 mmol) of triethylamine in 10 ml of dimethylformamide is heated overnight at 100° C. After this period of time, the suspension is poured into a mixture of 30 ml of water and 30 ml of ethyl acetate. The aqueous phase is separated and then extracted with 20 ml of ethyl acetate. The organic phases are combined, washed three times with 25 ml of water and then dried over sodium sulphate and concentrated under reduced pressure. 0.34 g of the expected product is thus obtained in the form of a solid which will be used as it is in the subsequent synthesis.

$^1$H NMR (DMSO D$_6$), δ (ppm): 8.95 (s, 1H); 8.21 (dxd, 1H); 6.41 (d, 1H); 5.85 (d, 1H); 4.62 (m, 1H); 4.37 (m, 2H); 3.9 (m, 2H).

2.2 3-Amino-6-(3-hydroxyazetidin-1-yl)pyridine

A suspension of 0.34 g (1.74 mmol) of 2-(3-hydroxyazetidin-1-yl)-5-nitropyridine, prepared in the preceding stage, and of 9 mg of Pd/C at 10% in 10 ml of ethanol is stirred vigorously at 20° C. under 5 atmospheres of hydrogen for 4 hours. After this period of time, the mixture is filtered through a celite buffer and then concentrated under reduced pressure. The resulting product is purified by silica column chromatography, elution being carried out with a mixture of dichloromethane and methanol. 0.1 g of the expected product is thus obtained, which product will be used as it is in the subsequent synthesis.

$^1$H NMR (DMSO D$_6$), δ (ppm): 7.58 (s, 1H); 6.91 (d, 1H); 6.22 (d, 1H); 5.48 (broad peak, 1H); 4.48 (broad peak, 3H); 3.98 (m, 2H); 3.49 (m, 2H).

2.3 N-[6-(3-Hydroxyazetidin-1-yl)pyridin-3-yl]-6-trimethylsilyl-1-[(3-fluorophenyl)methyl]-1H-indole-2-carboxamide (Compound No. 2)

114 mg (0.59 mmol) of N-(3-dimethylaminopropyl)-N'-ethylcarbodiimide hydrochloride (EDAC) and 81 mg (0.59 mmol) of 1-hydroxybenzotriazole (HOBT) are added to a solution, stirred at 20° C. under an inert atmosphere, of 0.2 g (0.59 mmol) of 6-trimethylsilyl-1-[(3-fluorophenyl)methyl]-1H-indole-2-carboxylic acid, prepared in stage 1.4, in 5 ml of DMF. The reaction mixture is stirred at ambient temperature for 15 minutes. 145 mg (0.88 mmol) of 3-amino-6-(3-hydroxyazetidin-1-yl)pyridine, prepared in stage 2.2, are subsequently added to the reaction mixture. After stirring at 20° C. for 20 hours, the reaction mixture is poured into a mixture of 30 ml of a saturated aqueous solution of NaHCO$_3$ and 30 ml of ethyl acetate. The resulting mixture is separated by settling out and the aqueous phase is extracted with 20 ml of ethyl acetate. The combined organic phases are washed three times with 30 ml of water, dried over sodium sulphate and then concentrated under reduced pressure. The product obtained is purified by silica column chromatography, elution being carried out with a mixture of dichloromethane and methanol. The solid obtained after evaporation of the solvent under reduced pressure is recrystallized from isopropyl ether. 175 mg of the expected product are thus isolated.

Mp=188-189° C.

$^1$H NMR (DMSO D$_6$), δ (ppm): 10.15 (s, 1H); 8.25 (d, 1H); 7.7 (dd, 1H); 7.6 (d, 1H); 7.55 (s, 1H); 7.3-7.18 (m, 3H); 7.0-6.75 (m, 3H); 6.3 (d, 1H); 5.85 (s, 2H); 5.5 (d, 1H); 4.45 (m, 1H); 4.0 (m, 2H); 3.5 (m, 2H); 0.15 (s, 9H).

EXAMPLE 3

Compound No. 3

N-[6-(Azetidin-1-yl)pyridin-3-yl]-5-trimethylsilyl-1-[(3-fluorophenyl)methyl]-1H-indole-2-carboxamide 3.1 1-Bromo-3-trimethylsilylbenzene 26.49 ml (42.39 mmol) of a solution of BuLi (1.5M/hexane) are added dropwise, with stirring, over 30 min, to a solution of 10 g (42.39 mmol) of 1,3-dibromobenzene in 80 ml of anhydrous Et$_2$O, cooled to −78° C. and maintained under a nitrogen atmosphere. After stirring for a further 30 min at −78° C., 5.96 ml (46.63 mmol) of TMSCl are introduced dropwise into the reaction mixture. The stirring is maintained at this temperature for 90 min and the reaction mixture is subsequently hydrolysed by adding 15 ml of water. The product is extracted with ethyl acetate (3×50 ml). The combined organic phases are washed with a saturated aqueous solution of NaCl (2×25 ml), dried over Na$_2$SO$_4$, filtered and evaporated under reduced pressure. The reaction crude is purified by silica gel column chromatography, elution being carried out with heptane, so as to isolate 9.3 g of the expected 1-bromo-3-trimethylsilylbenzene, in the form of a colourless oil.

$^1$H NMR (DMSO D$_6$), δ (ppm): 5.75 (s, 1H), 7.46 (m, 1H), 7.4 (m, 1H), 7.22 (t, 1H), 0.2 (s, 9H).

3.2 3-Trimethylsilylbenzaldehyde 16.36 ml (26.18 mmol) of BuLi (1.6N/hexane) are added dropwise, with stirring and over 30 min, to a solution of 5 g (21.89 mmol) of 1-bromo-3-trimethylsilylbenzene prepared according to the protocol described in stage 3.1, in 40 ml of anhydrous Et$_2$O, cooled to 0° C. and maintained under a nitrogen atmosphere. The stirring is continued at 0° C. for a further 30 min, and then maintained at ambient temperature for 90 min. 2.69 ml (34.91 mmol) of DMF, diluted in 17 ml of anhydrous Et$_2$O, are subsequently introduced into the reaction mixture. After stirring for 3 h at ambient temperature, the reaction mixture is hydrolysed at 0° C. by successive additions of 10 ml of a concentrated HCl solution and 100 ml of water. The product is extracted with 3×50 ml of CH$_2$Cl$_2$. The combined organic phases are washed with 100 ml of water, dried over Na$_2$SO$_4$, filtered and evaporated under reduced pressure. The reaction crude is purified by flash chromatography on a silica gel column, elution being carried out with a gradient of 10 to 20% of CH$_2$Cl$_2$ in heptane, to give 1.82 g of expected 3-trimethylsilyl-benzaldehyde in the form of a yellow oil.

$^1$H NMR (DMSO D$_6$), δ (ppm): 10.01 (s, 1H); 8.0 (s, 1H); 7.85 (d, 1H); 7.8 (d, 1H); 7.5 (dd, 1H) 0.3 (s, 9H)

3.3 Ethyl 2-azido-3-(3-trimethylsilylphenyl)propenoate

A mixture of 31.4 ml (87.5 mmol) of ethyl azidoacetate (at 34% in CH$_2$Cl$_2$) and 3.9 g (21.87 mmol) of 3-trimethylsilyl-benzaldehyde prepared according to the procedure described in stage 3.2, diluted in 3 ml of EtOH, is added dropwise to a solution of 2 g (87.5 mmol) of sodium in 30 ml of anhydrous EtOH, maintained under a nitrogen atmosphere and cooled to −10° C. The reaction mixture is stirred at 0° C. for 4 h. It is subsequently hydrolysed by adding, with vigorous stirring, 100 ml of an aqueous solution of NH$_4$Cl (30%). The aqueous phase is extracted with 3×50 ml of EtOAc. The combined organic phases are washed with water, dried over Na$_2$SO$_4$ and concentrated under reduced pressure. The reaction crude is purified by silica gel column chromatography, elution being carried out with an isocratic mixture of heptane and CH$_2$Cl$_2$ (80/20). 1.7 g of the expected ethyl 2-azido-3-(3-trimethylsilylphenyl)propenoate are thus isolated in the form of a yellow oil.

$^1$H NMR (DMSO D$_6$), δ (ppm): 7.9 (d, 1H); 7.8 (s, 1H); 7.4 (d, 1H); 7.3 (dd, 1H); 6.9 (s, 1H); 4.2 (q, 2H); 1.2 (t, 3H); 0.15 (s, 9H).

MS: [MH]$^+$=289.

3.4 Ethyl 5-trimethylsilyl-1H-indole-2-carboxylate 0.62 g (0.59 mmol) of the dirhodium(II) heptafluorobutyrate dimer complex is added to a solution of 1.7 g (5.90 mmol) of ethyl 2-azido-3-(3-trimethylsilylphenyl)propenoate prepared according to the procedure described in stage 3.3, in 25 ml of dry toluene, maintained under an inert atmosphere. The reaction mixture is stirred for 7 h at 40° C. A second portion of 0.62 g (0.59 mmol) of the dirhodium(II) heptafluorobutyrate dimer complex is added to the reaction mixture while maintaining the stirring and the heating at 40° C. for a further 1 h. After a return to ambient temperature, the reaction mixture is filtered over silica gel, elution being carried out with toluene. The filtrate is subsequently concentrated under reduced pressure. The greenish solid obtained is triturated several times in a minimum amount of heptane, until a white powder is obtained. The latter is dried under reduced pressure to give 0.87 g of the expected ethyl 5-trimethylsilyl-1H-indole-2-carboxylate in the form of a white powder.

Mp=114-115° C.

$^1$H NMR (DMSO D$_6$), δ (ppm): 11.7 (s, 1H); 7.7 (s, 1H); 7.35 (d, 1H); 7.25 (d, 1H); 7.0 (s, 1H); 4.2 (q, 2H); 1.2 (t, 3H); 0.15 (s, 9H).

LC-MS: 260 ([M−H]−, Rt=5.05 min.).

3.5 Ethyl 5-trimethylsilyl-1-[(3-fluorophenyl)methyl]-1H-indole-2-carboxylate 0.32 g (1.68 mmol) of 3-fluorobenzyl bromide and 100 mg (0.31 mmol) of tetrabutyl-ammonium bromide are added, slowly at ambient temperature, to a suspension of 0.4 g (1.53 mmol) of ethyl 5-trimethylsilyl-1H-indole-2-carboxylate, obtained according to the protocol described in stage 3.4, and of 0.64 g (4.59 mmol) of potassium carbonate in 15 ml of dry acetonitrile, maintained under an inert atmosphere. The reaction mixture is stirred at reflux for 2 h. After this period of time, the cooled suspension is filtered through a frit and rinsed with acetonitrile. The reaction crude obtained after evaporation of the filtrate under reduced pressure is purified by flash chromatography on a silica gel column, elution being carried out with a gradient of 5 to 15% of ether in heptane. 0.5 g of the expected ethyl 5-trimethylsilyl-1-[(3-fluorophenyl)methyl]-1H-indole-2-carboxylate is thus isolated.

Mp=80-82° C.

$^1$H NMR (CDCl$_3$), δ (ppm): 7.9 (s, 1H); 7.5-7.1 (m, 4H); 6.9 (m, 2H); 6.75 (m, 1H); 5.8 (s, 2H); 4.3 (q, 2H); 1.35 (t, 3H); 0.3 (s, 9H).

LC-MS: 370 ([M+H]+, Rt=6.22 min.).

3.6 5-Trimethylsilyl-1-[(3-fluorophenyl)methyl]-1H-indole-2-carboxylic acid (Compound No. IVb)

A solution of 0.6 g (1.62 mmol) of ethyl 5-trimethylsilyl-1-[(3-fluorophenyl)methyl]-1H-indole-2-carboxylate, obtained in stage 3.5, in 10 ml of absolute ethanol and 2.44 ml of 1N sodium hydroxide, is stirred at reflux for 4 hours. After this period of time, the reaction mixture is concentrated under reduced pressure and then taken up in 50 ml of water. The medium is acidified at pH 1 by successive additions of 1N hydrochloric acid. The precipitate is recovered by filtration, washed with water and then dried under reduced pressure. 0.53 g of the expected product is thus obtained, which product is used as it is in the subsequent stage.

Mp=177-178° C.

$^1$H NMR (DMSO D$_6$), δ (ppm): 13.1 (broad peak, 1H); 7.9 (s, 1H); 7.4 (d, 1H); 7.4 (m, 3H); 7.1 (m, 1H); 6.85 (m, 2H); 5.9 (s, 2H); 0.3 (s, 9H).

3.7 N-[6-(Azetidin-1-yl)pyridin-3-yl]-5-trimethylsilyl-1-[(3-fluorophenyl)methyl]-1H-indole-2-carboxamide (compound No. 3)

98 mg (0.51 mmol) of N-(3-dimethylaminopropyl)-N'-ethylcarbodiimide hydrochloride (EDC) and 69 mg (0.51 mmol) of 1-hydroxybenzotriazole (HOBt) are added to a solution, stirred at 20° C. under an inert atmosphere, of 0.16 g (0.47 mmol) of 5-trimethylsilyl-1-[(3-fluorophenyl)methyl]-1H-indole-2-carboxylic acid, prepared according to the protocol described in stage 3.6, in 10 ml of DMF. The reaction mixture is stirred at ambient temperature for 15 minutes. 84 mg (0.56 mmol) of 3-amino-6-(azetidin-1-yl)pyridine, prepared according to the protocol described in stage 1.6, are subsequently added to the reaction mixture. After stirring at 20° C. for 16 h, the reaction mixture is poured into a mixture of 30 ml of a saturated aqueous solution of NaHCO$_3$ and 30 ml of EtOAc. The aqueous phase is extracted with 20 ml of EtOAc. The combined organic phases are washed with 3×30 ml of water, dried over Na$_2$SO$_4$, and then concentrated under reduced pressure. The solid obtained after evaporation of the solvent under reduced pressure is washed with isopropyl ether at reflux, filtered under hot conditions and then dried under reduced pressure. 75 mg of the expected product are thus isolated.

Mp=212-213° C.

$^1$H NMR (DMSO D$_6$), δ (ppm): 10.1 (s, 1H); 8.2 (s, 1H); 7.75 (s, 1H); 7.7 (d, 1H); 7.4 (d, 1H); 7.3 (s, 1H); 7.35 (d, 1H); 7.2 (q, 1H); 6.9 (t, 1H); 6.8 (d, 1H); 6.75 (d, 1H); 6.25 (d, 1H); 5.8 (s, 2H); 3.8 (t, 4H); 2.2 (m, 2H); 0.15 (s, 9H)

LC-MS: 473 ([M+H]+, Rt=1.28 min.).

EXAMPLE 4

Compound No. 4

N-[6-(3-Hydroxyazetidin-1-yl)pyridin-3-yl]-5-trimethylsilyl-1-[(3-fluorophenyl)methyl]-1H-indole-2-carboxamide 123 mg (0.64 mmol) of N-(3-dimethylaminopropyl)-N'-ethylcarbodiimide hydrochloride (EDAC) and 87 mg (0.64 mmol) of 1-hydroxybenzotriazole (HOBT) are added to a solution, stirred at 20° C. under an inert atmosphere, of 0.2 g (0.59 mmol) of 5-trimethyl-silyl-1-[(3-fluorophenyl)methyl]-1H-indole-2-carboxylic acid, prepared according to the protocol described in stage 3.6, in 6 ml of DMF. The reaction mixture is stirred at ambient temperature for 15 minutes. 145 mg (0.88 mmol) of 3-amino-6-(3-hydroxyazetidin-1-yl)pyridine, prepared in stage 2.2, are subsequently added to the reaction mixture. After stirring at 20° C. for 16 hours, the reaction mixture is poured into a mixture of 30 ml of a saturated aqueous solution of NaHCO$_3$ and 30 ml of ethyl acetate. The resulting mixture is separated by settling out and the aqueous phase is extracted with 20 ml of ethyl acetate. The combined organic phases are washed three times with 30 ml of water, dried over sodium sulphate and then concentrated under reduced pressure. The product obtained is purified by silica column chromatography, elution being carried out with a mixture of dichloromethane and methanol. The solid obtained after evaporation of the solvent under reduced pressure is recrystallized from isopropyl ether. 200 mg of the expected product are thus isolated.

Mp=207-208° C.

$^1$H NMR (DMSO D$_6$), δ (ppm): 10.1 (s, 1H); 8.2 (s, 1H); 7.72 (s, 1H); 7.7 (d, 1H); 7.4 (d, 1H); 7.25 (m, 2H); 7.2 (m, 1H); 6.9 (m, 1H); 6.8 (m, 2H); 6.3 (d, 1H); 5.8 (s, 2H); 5.5 (d, 1H); 4.4 (m, 1H); 4.0 (m, 2H); 3.5 (m, 2H); 0.2 (s, 9H)

LC-MS: 489 ([M+H]+, Rt=1.25 min.).

EXAMPLE 5

Compound No. 5

N-[6-(Azetidin-1-yl)pyridin-3-yl]-7-trimethylsilyl-1-[(3-fluorophenyl)methyl]-1H-indole-2-carboxamide

5.1 Ethyl 7-trimethylsilyl-1H-indole-2-carboxylate 70 ml of xylene are brought to reflux in a three-necked flask surmounted by a condenser and a dropping funnel and maintained under an inert atmosphere. A solution of 0.7 g (2.42 mmol) of ethyl 2-azido-3-(3-trimethylsilylphenyl)propenoate prepared according to the procedure described in stage 3.3, in 1 ml of xylene, is subsequently added dropwise. The reaction mixture is refluxed for a further 1 h with stirring. After a return to ambient temperature, the reaction crude obtained after evaporation of the solvent under reduced pressure is purified by flash chromatography on a silica gel column, elution being carried out with a gradient of 0 to 20% of ethyl ether in heptane. Two regioisomeric products are thus isolated: 170 mg of ethyl 5-trimethylsilyl-1H-indole-2-carboxylate, in the form of a white powder, and 150 mg of the expected ethyl 7-trimethylsilyl-1H-indole-2-carboxylate in the form of an oil.

$^1$H NMR (DMSO D$_6$), δ (ppm): 10.8 (s, 1H); 7.7 (d, 1H); 7.4 (d, 1H); 7.2 (s, 1H); 7.1 (m, 1H); 4.3 (q, 2H); 1.3 (t, 3H); 0.4 (s, 9H).

LC-MS: 260 ([M−H]−, Rt=5.48 min.).

5.2 Ethyl 7-trimethylsilyl-1-[(3-fluorophenyl)methyl]-1H-indole-2-carboxylate 0.42 ml (3.44 mmol) of 3-fluorobenzyl bromide is added, slowly at ambient temperature, to a suspension of 0.75 g (2.87 mmol) of ethyl 7-trimethylsilyl-1H-indole-2-carboxylate, obtained according to the protocol described in stage 5.1, and of 1.18 g (8.61 mmol) of potassium carbonate in 50 ml of dry acetonitrile, maintained under an inert atmosphere. The reaction mixture is stirred at reflux for 18 h. After this period of time, the cooled suspension is filtered through a frit and then rinsed with acetonitrile. The reaction crude obtained after evaporation of the filtrate under reduced pressure is purified by flash chromatography on a silica gel column, elution being carried out with a gradient of 10 to 50% of dichloromethane in heptane. 0.67 g of the expected ethyl 7-trimethylsilyl-1-[(3-fluorophenyl)methyl]-1H-indole-2-carboxylate is thus isolated.

$^1$H NMR (DMSO D$_6$), δ (ppm): 7.8 (d, 1H); 7.5 (d, 1H); 7.2 (m, 2H); 6.95 (m, 2H); 6.35 (m, 2H); 5.9 (s, 2H); 4.1 (q, 2H); 1.1 (t, 3H); 0.2 (s, 9H).

LC-MS: 370 ([M+H]+, Rt=6.15 min.).

5.3 7-Trimethylsilyl-1-[(3-fluorophenyl)methyl]-1H-indole-2-carboxylic acid (Compound No. IVc)

0.23 g (4.06 mmol) of potassium hydroxide is added to a solution of 0.5 g (1.35 mmol) of ethyl 7-trimethylsilyl-1-[(3-fluorophenyl)methyl]-1H-indole-2-carboxylate, obtained according to the protocol described in stage 5.2, in 30 ml of a mixture (v/v/v) of methanol, water and dioxane. After stirring at reflux for three hours, the reaction mixture is one-third concentrated under reduced pressure and then taken up in 10 ml of water. The medium is acidified at pH 1 by successive additions of 1N hydrochloric acid. The precipitate is recovered by filtration, washed with water and then dried under reduced pressure. 0.37 g of the expected product is thus isolated, which product is used as it is in the subsequent stage.

$^1$H NMR (DMSO D$_6$), δ (ppm): 12.6 (broad peak, 1H); 7.6 (d, 1H); 7.3 (d, 1H); 7.2 (s, 1H); 7.0 (m, 2H); 6.75 (m, 1H); 6.2 (m, 1H); 6.1 (d, 1H); 5.8 (s, 2H); 0.05 (s, 9H).

LC-MS: 342 ([M+H]+, Rt=1.48 min.).

5.4 N-[6-(Azetidin-1-yl)pyridin-3-yl]-7-trimethylsilyl-1-[(3-fluorophenyl)methyl]-1H-indole-2-carboxamide (Compound No. 5)

0.28 g (1.46 mmol) of N-(3-dimethylaminopropyl)-N'-ethylcarbodiimide hydrochloride (EDC) and 0.2 g (1.46 mmol) of 1-hydroxybenzotriazole (HOBt) are added to a solution, stirred at 20° C. under an inert atmosphere, of 0.5 g (1.46 mmol) of 7-trimethyl-silyl-1-[(3-fluorophenyl)methyl]-1H-indole-2-carboxylic acid, prepared according to the protocol described in stage 5.3, in 10 ml of DMF. The reaction mixture is stirred at ambient temperature for 20 minutes. 0.33 g (2.20 mmol) of 3-amino-6-(azetidin-1-yl)pyridine, prepared according to the protocol described in stage 1.6, is subsequently added to the reaction mixture. After stirring at 20° C. for 18 h, the reaction mixture is poured into a mixture of 30 ml of a saturated aqueous solution of NaHCO$_3$ and 30 ml of EtOAc. The aqueous phase is extracted with 20 ml of EtOAc. The combined organic phases are washed with 3×30 ml of water, dried over Na$_2$SO$_4$, then concentrated under reduced pressure. The solid obtained after evaporation of the solvent under reduced pressure is purified by flash chromatography on a silica gel column, elution being carried out with a gradient of 2 to 10% of MeOH in CH$_2$Cl$_2$. The isolated product is subsequently precipitated, then washed with a mixture of hexane and isopropyl ether at reflux, filtered under hot conditions, and then dried under reduced pressure. 147 mg of the expected product are thus isolated.

Mp=160-162° C.

$^1$H NMR (DMSO D$_6$), δ (ppm): 9.9 (s, 1H); 8.0 (s, 1H); 7.7 (d, 1H); 7.5 (d, 1H); 7.3 (d, 1H); 7.2 (s, 1H); 7.0 (m, 2H); 6.8 (m, 1H); 6.25 (d, 1H); 6.15 (m, 2H); 5.8 (s, 2H); 3.7 (t, 4H); 2.1 (m, 2H); 0.15 (s, 9H).

LC-MS: 473 ([M+H]+, Rt=1.25 min.).

EXAMPLE 6

Compound No. 6

N-[6-(3-Hydroxyazetidin-1-yl)pyridin-3-yl]-7-trimethylsilyl-1-[(3-fluorophenyl)methyl]-1H-indole-2-carboxamide (Compound No. 6)

Compound No. 6 was prepared according to a process similar to that described in stage 5.4, by reacting 0.15 g (0.44 mmol) of 7-trimethylsilyl-1-[(3-fluorophenyl)methyl]-1H-indole-2-carboxylic acid, prepared according to the protocol described in stage 5.3, with 109 mg (0.66 mmol) of 3-amino-6-(3-hydroxyazetidin-1-yl)pyridine, prepared according to the protocol described in stage 2.2, in the presence of 87 mg (0.44 mmol) of N-(3-dimethylaminopropyl)-N'-ethylcarbodiimide hydrochloride (EDAC) and of 61 mg (0.44 mmol) of 1-hydroxybenzotriazole (HOBT) in 5 ml of dimethylformamide. 27 mg of the expected product are obtained.

$^1$H NMR (DMSO D$_6$), δ (ppm): 9.9 (s, 1H); 8.0 (s, 1H); 7.7 (d, 1H); 7.5 (d, 1H); 7.3 (d, 1H); 7.2 (s, 1H); 7.0 (m, 2H); 6.8 (m, 1H); 6.25 (d, 1H); 6.15 (m, 2H); 5.8 (s, 2H); 5.5 (d, 1H); 4.4 (m, 1H); 4.0 (m, 2H); 3.5 (m, 2H); 0.15 (s, 9H).

LC-MS: 489 ([M+H]+, Rt=1.3 min.).

Mp=215-217° C.

EXAMPLE 7

Compound No. 7

N-[6-(Dimethylamino)pyridin-3-yl]-5-trimethylsilyl-1-[(3-fluorophenyl)methyl]-1H-indole-2-carboxamide Compound No. 7 was prepared according to a process similar to that described in stage 5.4, by reacting 0.3 g (0.88 mmol) of 5-trimethylsilyl-1-[(3-fluorophenyl)methyl]-1H-indole-2-carboxylic acid, prepared according to the protocol described in stage 3.6, with 181 mg (1.32 mmol) of 3-amino-6-(dimethylamino)pyridine in the presence of 185 mg (0.97 mmol) of N-(3-dimethylaminopropyl)-N'-ethylcarbodiimide hydrochloride (EDAC) and of 131 mg (0.97 mmol) of 1-hydroxybenzotriazole (HOBT) in 10 ml of dimethylformamide. The product obtained is purified by silica column chromatography, elution being carried out with a mixture of dichloromethane and acetone. The solid obtained after evaporation of the solvent under reduced pressure is recrystallized from isopropyl alcohol. 200 mg of the expected product are thus isolated.

Mp=204-205° C.

$^1$H NMR (DMSO D$_6$), δ (ppm): 10.2 (s, 1H); 8.4 (s, 1H); 7.9 (m, 2H); 7.55 (d, 1H); 7.4 (m, 2H); 7.3 (m, 1H); 7.0 (m, 1H); 6.9 (m, 2H); 6.65 (d, 1H); 5.9 (s, 2H); 3.0 (s, 6H); 0.25 (s, 9H).

LC-MS: 461 ([M–H]–, Rt=1.3 min.).

EXAMPLE 8

Compound No. 8

N-[6-(Azetidin-1-yl)pyridin-3-yl]-5-(ethyl)dimethylsilyl-1-[(3-fluorophenyl)methyl]-1H-indole-2-carboxamide

8.1 Ethyl 5-iodo-1-[(3-fluorophenyl)methyl]-1H-indole-2-carboxylate

A solution of 2.0 g (6.03 mmol) of ethyl 5-iodo-1H-indole-2-carboxylate (obtained according to the protocol described in the literature, Synthetic Communications (2003) 33(14), 2423-2427) in 10 ml of dry DMF is added dropwise, at 0° C., to a suspension of 0.26 g (6.63 mmol) of sodium hydride (60%) in 10 ml of dry DMF, maintained under an inert atmosphere. The reaction mixture is stirred at ambient temperature for one hour. 1.37 g (7.24 mmol) of 3-fluorobenzyl bromide are subsequently added, dropwise, at 0° C. The reaction mixture is then stirred at ambient temperature for 18 h and then diluted with 200 ml of a mixture of water and ethyl acetate (1/1). The resulting mixture is separated by settling out and the aqueous phase is extracted with 2×30 ml of ethyl acetate. The combined organic phases are washed three times with water, dried over sodium sulphate, filtered and concentrated under reduced pressure. The resulting oil is purified by silica gel column chromatography, elution being carried out with a mixture of heptane and ethyl acetate. 1.87 g of the expected product are isolated.

$^1$H NMR (DMSO D$_6$), δ (ppm): 8.15 (s, 1H); 7.6 (d, 1H); 7.5 (d, 1H); 7.35 (s, 1H); 7.3 (m, 1H); 7.1 (m, 1H); 6.85 (m, 2H); 5.9 (s, 2H); 4.3 (q, 2H); 1.3 (t, 3H).

LC-MS: 424 ([M+H]+, Rt=1.65).

8.2 5-Iodo-1-[(3-fluorophenyl)methyl]-1H-indole-2-carboxylic acid

A solution of 1.00 g (2.36 mmol) of ethyl 5-iodo-1-[(3-fluorophenyl)methyl]-1H-indole-2-carboxylate, obtained in stage 8.1, and of 0.4 g (7.09 mmol) of potassium hydroxide, in 30 ml of a mixture (v/v/v) of methanol, dioxane and water, is stirred at reflux for 3 hours. After this period of time, the reaction mixture is concentrated under reduced pressure and then taken up in 10 ml of water. The medium is acidified at pH 1 by successive additions of 1N hydrochloric acid. The precipitate is recovered by filtration, washed with water and then dried under reduced pressure. 0.69 g of the expected product is thus isolated, which product is used as it is in the subsequent stage.

$^1$H NMR (DMSO D$_6$), δ (ppm): 13.2 (broad peak, 1H); 8.1 (s, 1H); 7.5 (d, 1H); 7.4 (d, 1H); 7.25 (m, 2H); 7.0 (m, 1H); 6.8 (m, 2H); 5.8 (s, 2H).

LC-MS: 394 ([M−H]−, Rt=3.5).

8.3 N-[6-(Azetidin-1-yl)pyridin-3-yl]-5-iodo-1-[(3-fluorophenyl)methyl]-1H-indole-2-carboxamide 0.29 g (1.52 mmol) of N-(3-dimethylaminopropyl)-N'-ethylcarbodiimide hydrochloride (EDAC) and 0.2 g (1.52 mmol) of 1-hydroxybenzotriazole (HOBT) are added to a solution, stirred at 20° C. under an inert atmosphere, of 0.6 g (1.52 mmol) of 5-iodo-1-[(3-fluorophenyl)methyl]-1H-indole-2-carboxylic acid, prepared in stage 8.2, in 15 ml of DMF. The reaction mixture is stirred at ambient temperature for 20 minutes. 0.25 g (1.67 mmol) of 3-amino-6-(azetidin-1-yl) pyridine, prepared according to the protocol described in stage 1.6, is subsequently added to the reaction mixture. After stirring at 20° C. for 18 hours, the reaction mixture is poured into a mixture of 50 ml of water and 50 ml of ethyl acetate. The resulting mixture is separated by settling out and the aqueous phase is extracted with 20 ml of ethyl acetate. The combined organic phases are washed three times with 30 ml of water, dried over sodium sulphate and then concentrated under reduced pressure. The isolated product is subsequently precipitated, then washed with isopropyl ether at reflux, filtered under hot conditions, and then dried under reduced pressure. 0.47 g of the expected product is thus isolated.

$^1$H NMR (DMSO D$_6$), δ (ppm): 10.3 (s, 1H); 8.35 (s, 1H); 8.2 (s, 1H); 7.85 (d, 1H); 7.55 (d, 1H); 7.45 (d, 1H); 7.3 (m, 2H); 7.05 (m, 1H); 6.9 (m, 2H); 6.4 (d, 1H); 5.9 (s, 2H); 3.9 (t, 4H); 2.3 (quint., 2H).

LC-MS: 527 ([M+H]+, Rt=5.07).

8.4 N-[6-(Azetidin-1-yl)pyridin-3-yl]-5-(ethyl)dimethylsilyl-1-[(3-fluorophenyl)methyl]-1H-indole-2-carboxamide (compound No. 8)

27 mg (0.31 mmol) of (ethyl)dimethylsilane and 15 mg (0.03 mmol) of bis(tri-tert-butylphosphine)palladium are added to a suspension of 0.15 g (0.28 mmol) of N-[6-(azetidin-1-yl)pyridin-3-yl]-5-iodo-1-[(3-fluorophenyl)methyl]-1H-indole-2-carboxamide, prepared according to the protocol described in stage 8.3, and of 0.18 g (0.85 mmol) of potassium triphosphate in 2 ml of dry 1-methyl-2-pyrrolidinone (NMP), maintained under an inert atmosphere. The reaction mixture is then stirred at ambient temperature under an inert atmosphere for 6 h and then diluted with 40 ml of a mixture of water and ethyl acetate (1/1). The resulting mixture is separated by settling out and the aqueous phase is extracted with 2×10 ml of ethyl acetate. The combined organic phases are dried over sodium sulphate, filtered and concentrated under reduced pressure. The resulting oil is purified by silica gel column chromatography, elution being carried out with a mixture of heptane and ethyl acetate. 108 mg of the expected product are isolated.

Mp=188-189° C.

$^1$H NMR (DMSO D$_6$), δ (ppm): 10.25 (s, 1H); 8.4 (s, 1H); 7.85 (m, 2H); 7.6 (d, 1H); 7.35 (m, 3H); 7.1 (m, 1H); 6.9 (m, 2H); 6.4 (d, 1H); 5.9 (s, 2H); 3.9 (t, 4H); 2.3 (quint., 2H); 0.95 (t, 3H); 0.75 (q, 2H); 0.3 (s, 6H).

LC-MS: 487 ([M+H]+, Rt=1.37).

EXAMPLE 9

Compound No. 9

N-[6-(Azetidin-1-yl)pyridin-3-yl]-5-(cyclohexyl) dimethylsilyl-1-[(3-fluorophenyl)methyl]-1H-indole-2-carboxamide (Compound No. 9)

Compound No. 9 was prepared according to a process similar to that described in stage 8.4, by reacting 0.15 g (0.28 mmol) of N-[6-(azetidin-1-yl)pyridin-3-yl]-5-iodo-1-[(3-fluorophenyl)methyl]-1H-indole-2-carboxamide, prepared according to the protocol described in stage 8.3, with 44 mg (0.31 mmol) of (cyclohexyl)dimethylsilane in the presence of 0.18 g (0.85 mmol) of potassium triphosphate and of 15 mg (0.03 mmol) of bis(tri-tert-butylphosphine)palladium in 2 ml of dry 1-methyl-2-pyrrolidinone (NMP). 93 mg of the expected product are obtained in the form of a white solid.

Mp=202-203° C.

$^1$H NMR (DMSO D$_6$), δ (ppm): 10.25 (s, 1H); 8.4 (s, 1H); 7.8 (m, 2H); 7.5 (d, 1H); 7.35 (m, 3H); 7.0 (m, 1H); 6.9 (m, 2H); 6.4 (d, 1H); 5.9 (s, 2H); 3.9 (t, 4H); 2.3 (quint., 2H); 1.65 (m, 5H); 1.3-0.7 (m, 6H); 0.25 (s, 6H).

LC-MS: 541 ([M+H]+, Rt=1.56).

EXAMPLE 10

Compound No. 10

N-[6-(Azetidin-1-yl)pyridin-3-yl]-6-trimethylsilyl-1-[[(3-trifluoromethyl)phenyl]methyl]-1H-indole-2-carboxamide

10.1 Ethyl 6-trimethylsilyl-1-[[(3-trifluoromethyl)phenyl]methyl]-1H-indole-2-carboxylate 0.52 ml (3.83 mmol) of 3-(trifluoromethyl)phenylmethanol and 0.92 g (3.83 mmol) of (cyanomethylene)tributylphosphorane (CMBP) are added, at ambient temperature, to a solution of 0.5 g (1.91 mmol) of ethyl 6-trimethylsilyl-1H-indole-2-carboxylate, obtained according to the protocol described in stage 1.2, in 8 ml of dry toluene, maintained under an inert atmosphere. The reaction mixture is stirred at 110° C. for 15 hours and then concentrated to dryness. The reaction crude is subsequently purified by successive rounds of flash chromatography on a silica gel column, to give 0.72 g of expected ethyl 6-trimethylsilyl-1-[[(3-trifluoromethyl)phenyl]methyl]-1H-indole-2-carboxylate in the form of an oil.

$^1$H NMR (DMSO D$_6$), δ (ppm): 7.49-7.45 (m, 2H); 7.36-7.33 (m, 2H); 7.25 (t, 1H); 7.12 (s, 1H); 7.04-7.00 (m, 2H); 5.73 (s, 2H); 4.04 (q, 2H); 1.03 (t, 3H); 0.00 (s, 9H).

LC-MS: 420 ([M+H]+, Rt=3.57).

10.2 6-Trimethylsilyl-1-[[(3-trifluoromethyl)phenyl]methyl]-1H-indole-2-carboxylic acid (Compound No. IVd)

A solution of 0.125 g (2.18 mmol) of potassium hydroxide in 1 ml of water is added to a solution of 0.31 g (0.73 mmol) of ethyl 6-trimethylsilyl-1-[[(3-trifluoromethyl)phenyl]methyl]-1H-indole-2-carboxylate, obtained in stage 10.1, in 10 ml of ethanol. After stirring at 85° C. for two hours, the reaction mixture is concentrated under reduced pressure and then taken up in 10 ml of water. The medium is acidified at pH 5 by successive additions of 1N hydrochloric acid. The precipitate is recovered by filtration, washed with water and then dried under reduced pressure. 0.24 g of the expected product is thus isolated, which product is used as it is in the subsequent stage.

$^1$H NMR (DMSO D$_6$), δ (ppm): 13.2 (broad peak, 1H); 7.7 (m, 2H); 7.6 (m, 2H); 7.5 (m, 1H); 7.3 (m, 3H); 6.0 (s, 2H); 1.2 (s, 9H).

10.3 N-[6-(Azetidin-1-yl)pyridin-3-yl]-6-trimethylsilyl-1-[[(3-trifluoromethyl)phenyl]methyl]-1H-indole-2-carboxamide (Compound No. 10)

Compound No. 10 was prepared according to a process similar to that described in stage 8.3, by reacting 0.11 g (0.28 mmol) of 6-trimethylsilyl-1-[[(3-trifluoromethyl)phenyl]methyl]-1H-indole-2-carboxylic acid, prepared according to the protocol described in stage 10.2, with 46 mg (0.31 mmol) of 3-amino-6-(azetidin-1-yl)pyridine, prepared according to the protocol described in stage 1.6, in the presence of 59 mg (0.31 mmol) of N-(3-dimethylaminopropyl)-N'-ethylcarbodiimide hydrochloride (EDAC) and 45 mg (0.31 mmol) of 1-hydroxybenzotriazole (HOBT) in 2 ml of dimethylformamide. 200 mg of the expected product are obtained.

Mp=167-168° C.

$^1$H NMR (DMSO D$_6$), δ (ppm): 10.25 (s, 1H); 8.35 (d, 1H); 7.85 (dd, 1H); 7.7 (m, 2H); 7.65 (s, 1H); 7.6 (m, 1H); 7.5 (t, 1H); 7.45 (m, 1H); 7.35 (s, 1H); 7.25 (d, 1H); 6.4 (d, 1H); 6.0 (s, 2H); 3.95 (t, 4H); 2.3 (m, 2H); 0.2 (s, 9H).

LC-MS: 523 ([M+H]+, Rt=1.42 min.).

EXAMPLE 11

Compound No. 11

N-[6-(3-Hydroxyazetidin-1-yl)pyridin-3-yl]-6-trimethylsilyl-1-[[(3-trifluoromethyl)phenyl]methyl]-1H-indole-2-carboxamide (Compound No. 11)

Compound No. 11 was prepared according to a process similar to that described in stage 8.3, by reacting 0.11 g (0.28 mmol) of 6-trimethylsilyl-1-[[(3-trifluoromethyl)phenyl]methyl]-1H-indole-2-carboxylic acid, prepared according to the protocol described in stage 10.2, with 51 mg (0.31 mmol) of 3-amino-6-(3-hydroxyazetidin-1-yl)pyridine, prepared according to the protocol described in stage 2.2, in the presence of 59 mg (0.31 mmol) of N-(3-dimethylaminopropyl)-N'-ethylcarbodiimide (EDAC) and 45 mg (0.31 mmol) of 1-hydroxybenzotriazole (HOBT) in 2 ml of dimethylformamide. 0.21 g of the expected product is obtained.

Mp=183-184° C.

$^1$H NMR (DMSO D$_6$), δ (ppm): 10.3 (s, 1H); 8.4 (d, 1H); 7.85 (m, 1H); 7.7 (m, 2H); 7.65 (s, 1H); 7.6 (m, 1H); 7.5 (t, 1H); 7.45 (m, 1H); 7.35 (s, 1H); 7.25 (d, 1H); 6.4 (d, 1H); 6.0 (s, 2H); 5.6 (d, 1H); 4.6 (m, 1H); 4.15 (m, 2H); 3.65 (m, 2H); 0.25 (s, 9H).

LC-MS: 539 ([M+H]+, Rt=1.37 min.).

EXAMPLE 12

Compound No. 12

N-[6-(Azetidin-1-yl)pyridin-3-yl]-5-(diphenyl)methylsilyl-1-[(3-fluorophenyl)methyl]-1H-indole-2-carboxamide Compound No. 12 was prepared according to a process similar to that described in stage 8.4, by reacting 0.15 g (0.28 mmol) of N-[6-(azetidin-1-yl)pyridin-3-yl]-5-iodo-1-[(3-fluorophenyl)methyl]-1H-indole-2-carboxamide, prepared according to the protocol described in stage 8.3, with 167 mg (0.84 mmol) of diphenylmethylsilane in the presence of 0.18 g (0.84 mmol) of potassium triphosphate and of 15 mg (0.03 mmol) of bis(tri-tert-butylphosphine)palladium in 2 ml of dry 1-methyl-2-pyrrolidinone (NMP). 19 mg of the expected product are obtained.

Mp=98-100° C.

$^1$H NMR (DMSO D$_6$), δ (ppm): 10.25 (s, 1H); 8.4 (s, 1H); 7.85 (m, 2H); 7.65-7.25 (m, 14H); 7.05 (m, 1H); 6.95 (m, 2H); 6.4 (d, 1H); 5.9 (s, 2H); 3.95 (m, 4H); 2.3 (m, 2H); 0.9 (s, 3H).

LC-MS: 597 ([M+H]+, Rt=1.51).

EXAMPLE 13

Compound No. 13

N-[6-(Azetidin-1-yl)pyridin-3-yl]-5-trimethylsilyl-1-[[(3-trifluoromethyl)phenyl]methyl]-1H-indole-2-carboxamide (compound No. 13)

13.1 Ethyl 5-trimethylsilyl-1-[[(3-trifluoromethyl)phenyl]methyl]-1H-indole-2-carboxylate 0.51 ml (3.749 mmol) of 3-(trifluoromethyl)phenylmethanol and 0.9 g (3.749 mmol) of (cyanomethylene)tributylphosphorane (CMBP) are added, at ambient temperature, to a solution of 0.49 g (1.87 mmol) of ethyl 5-trimethylsilyl-1H-indole-2-carboxylate, obtained according to the protocol described in stage 3.4, in 8 ml of dry toluene, maintained under an inert atmosphere. The reaction mixture is stirred at 110° C. for 15 hours and then concentrated to dryness. The reaction crude is subsequently purified by flash chromatography on a silica gel column, elution being carried out with a mixture of hexane and ethyl acetate, to give 0.73 g of the expected ethyl 5-trimethylsilyl-1-[[(3-trifluoromethyl)phenyl]methyl]-1H-indole-2-carboxylate.

$^1$H NMR (DMSO D$_6$), δ (ppm): 7.90 (s, 1H); 7.62-7.57 (m, 2H); 7.51-7.43 (m, 3H); 7.40 (s, 1H); 7.17 (d, 1H); 5.92 (s, 2H); 4.28 (q, 2H); 1.26 (t, 3H); 0.27 (s, 9H).

LC-MS: 420 ([M+H]+, Rt=3.62).

13.2 5-Trimethylsilyl-1-[[(3-trifluoromethyl)phenyl]methyl]-1H-indole-2-carboxylic acid (Compound No. IVe)

A solution of 0.125 g (2.18 mmol) of potassium hydroxide in 1 ml of water is added to a solution of 0.31 g (0.73 mmol) of ethyl 5-trimethylsilyl-1-[[(3-trifluoromethyl)phenyl]methyl]-1H-indole-2-carboxylate, obtained in stage 13.1, in 10 ml of ethanol. After stirring at 85° C. for two hours, the reaction mixture is concentrated under reduced pressure and then taken up in 10 ml of water. The medium is acidified at pH 5 by successive additions of 1N hydrochloric acid. The precipitate is recovered by filtration, washed with water and then dried under reduced pressure. 0.22 g of the expected product is thus isolated, which product is used as it is in the subsequent stage.

$^1$H NMR (DMSO D$_6$), δ (ppm): 12.9 (broad peak, 1H); 7.8 (s, 1H); 7.5 (m, 2H); 7.4 (m, 2H); 7.3 (d, 1H); 7.2 (s, 1H); 7.1 (d, 1H); 5.85 (s, 2H); 1.2 (s, 9H).

13.3 N-[6-(Azetidin-1-yl)pyridin-3-yl]-5-trimethylsilyl-1-[[(3-trifluoromethyl)phenyl]methyl]-1H-indole-2-carboxamide (Compound No. 13)

Compound No. 13 was prepared according to a process similar to that described in stage 8.3, by reacting 0.105 g (0.27 mmol) of 5-trimethylsilyl-1-[[(3-trifluoromethyl)phenyl]methyl]-1H-indole-2-carboxylic acid, prepared according to the protocol described in stage 13.2, with 44 mg (0.30 mmol) of 3-amino-6-(azetidin-1-yl)pyridine, prepared according to the protocol described in stage 1.6, in the presence of 57 mg (0.30 mmol) of N-(3-dimethylaminopropyl)-N'-ethylcarbodiimide hydrochloride (EDAC) and 43 mg (0.30 mmol) of 1-hydroxybenzotriazole (HOBT) in 6 ml of dimethylformamide. 95 mg of the expected product are obtained.

Mp=199-200° C.

$^1$H NMR (DMSO D$_6$), δ (ppm): 10.25 (s, 1H); 8.3 (s, 1H); 7.9 (s, 1H); 7.8 (d, 1H); 7.55 (m, 3H); 7.5 (m, 1H); 7.4 (m, 2H); 7.3 (d, 1H); 6.3 (d, 1H); 5.9 (s, 2H); 3.9 (t, 4H); 2.3 (quint., 2H); 0.25 (s, 9H).

LC-MS: 523 ([M+H]+, Rt=1.50 min).

EXAMPLE 14

Compound No. 14

N-[6-(3-Hydroxyazetidin-1-yl)pyridin-3-yl]-5-trimethylsilyl-1-[[(3-trifluoromethyl)phenyl]methyl]-1H-indole-2-carboxamide (Compound No. 14)

Compound No. 14 was prepared according to a process similar to that described in stage 8.3, by reacting 0.1 g (0.26 mmol) of 5-trimethylsilyl-1-[[(3-trifluoromethyl)phenyl]methyl]-1H-indole-2-carboxylic acid, prepared according to the protocol described in stage 13.2, with 46 mg (0.28 mmol) of 3-amino-6-(3-hydroxyazetidin-1-yl)pyridine, prepared according to the protocol described in stage 2.2, in the presence of 54 mg (0.28 mmol) of N-(3-dimethylaminopropyl)-N'-ethylcarbodiimide hydrochloride (EDAC) and 41 mg (0.28 mmol) of 1-hydroxybenzotriazole (HOBT) in 6 ml of dimethylformamide. 100 mg of the expected product are obtained.

Mp=217-218° C.

$^1$H NMR (DMSO D$_6$), δ (ppm): 10.25 (s, 1H); 8.2 (d, 1H); 7.75 (s, 1H); 7.7 (dd, 1H); 7.45-7.35 (m, 4H); 7.5 (m, 1H); 7.3 (m, 2H); 7.2 (m, 1H); 6.3 (d, 1H); 5.85 (s, 2H); 5.45 (d, 1H); 4.4 (m, 1H); 4.0 (m, 2H); 3.55 (m, 2H); 0.0 (s, 9H).

LC-MS: 539 ([M+H]+, Rt=1.40 min.).

EXAMPLE 15

Compound No. 15

N-[6-(3-Hydroxyazetidin-1-yl)pyridin-3-yl]-6-trimethylsilyl-1-[(pyridin-4-yl)methyl]-1H-indole-2-carboxamide (Compound No. 15)

15.1. Ethyl 6-trimethylsilyl-1-[(4-pyridinyl)methyl)]-1H-indole-2-carboxylate 0.42 g (3.82 mmol) of 4-pyridinylmethanol and 0.92 g (3.826 mmol) of (cyano-methylene)tributylphosphorane (CMBP) are added, at ambient temperature, to a solution of 0.5 g (1.91 mmol) of ethyl 6-trimethylsilyl-1H-indole-2-carboxylate, obtained according to the protocol described in stage 1.2, in 8 ml of dry toluene, maintained under an inert atmosphere. The reaction mixture is stirred at 110° C. for 15 hours and then concentrated to dryness. The reaction crude is subsequently purified by flash chromatography on a silica gel column, elution being carried out with a mixture of heptane and ethyl acetate, to give 0.644 g of the expected ethyl 6-trimethylsilyl-1-[(pyridin-4-yl)methyl]-1H-indole-2-carboxylate in the form of a yellow solid.

$^1$H NMR (DMSO D$_6$), δ (ppm): 8.2 (d, 2H); 7.49 (d, 1H); 7.42 (s, 1H); 7.15 (s, 1H); 7.05 (d, 1H); 6.70 (d, 2H); 5.68 (s, 2H); 4.01 (q, 2H); 1.01 (t, 3H); 0.00 (s, 9H).

LC-MS: 353 ([M+H]+, Rt=2.63).

15.2 6-Trimethylsilyl-1-[(4-pyridinyl)methyl)]-1H-indole-2-carboxylic acid (Compound No. IVf)

A solution of 0.11 g (1.87 mmol) of potassium hydroxide in 1 ml of water is added to a solution of 0.22 g (0.62 mmol) of ethyl 6-trimethylsilyl-1-[(4-pyridinyl)methyl)]-1H-indole-2-carboxylate, obtained in stage 15.1, in 10 ml of ethanol. After stirring at 85° C. for two hours, the reaction mixture is concentrated under reduced pressure and then taken up in 10 ml of water. The medium is acidified at pH 5 by successive additions of 1N hydrochloric acid. The precipitate is recovered by filtration, washed with water and then dried under reduced pressure. 0.19 g of the expected product is thus isolated, which product is used as it is in the subsequent stage.

$^1$H NMR (DMSO D$_6$), δ (ppm): 8.2 (d, 2H); 7.4 (d, 1H); 7.3 (s, 1H); 7.0 (d, 1H); 6.9 (s, 1H); 6.8 (d, 2H); 5.8 (s, 2H); 0.95 (s, 9H).

15.3 N-[6-(3-Hydroxyazetidin-1-yl)pyridin-3-yl]-6-trimethylsilyl-1-[(pyridin-4-yl)methyl]-1H-indole-2-carboxamide (Compound No. 15)

Compound No. 15 was prepared according to a process similar to that described in stage 8.3, by reacting 94 mg (0.29 mmol) of 6-trimethylsilyl-1-[(4-pyridinyl)methyl)]-1H-indole-2-carboxylic acid, prepared according to the protocol described in stage 15.2, with 53 mg (0.32 mmol) of 3-amino-6-(3-hydroxyazetidin-1-yl)pyridine, prepared according to the protocol described in stage 2.2, in the presence of 61 mg (0.32 mmol) of N-(3-dimethylaminopropyl)-N'-ethylcarbodiimide hydrochloride (EDAC) and 46 mg (0.32 mmol) of 1-hydroxybenzotriazole (HOBT) in 2 ml of dimethylformamide. 80 mg of the expected product is obtained.

$^1$H NMR (DMSO D$_6$), δ (ppm): 10.2 (s, 1H); 8.45 (d, 2H); 8.35 (s, 1H); 7.85 (d, 1H); 7.75 (d, 1H); 7.6 (s, 1H); 7.45 (s, 1H); 7.3 (d, 1H); 7.0 (d, 2H); 6.4 (d, 1H); 5.95 (s, 2H); 5.6 (d, 1H); 4.6 (m, 1H); 4.15 (m, 2H); 3.65 (m, 2H); 0.25 (s, 9H).

LC-MS: 472 ([M+H]+, Rt=0.91 min.).

EXAMPLE 16

Compound No. 16

N-[6-(Azetidin-1-yl)pyridin-3-yl]-6-trimethylsilyl-1-[(pyridin-4-yl)methyl]-1H-indole-2-carboxamide Compound No. 16 was prepared according to a process similar to that described in stage 8.3, by reacting 95 mg (0.29 mmol) of 6-trimethylsilyl-1-[(4-pyridinyl)methyl)]-1H-indole-2-carboxylic acid, prepared according to the protocol described in stage 15.2, with 48 mg (0.32 mmol) of 3-amino-6-(azetidin-1-yl)pyridine, prepared according to the protocol described in stage 1.6, in the presence of 62 mg (0.32 mmol) of N-(3-dimethylaminopropyl)-N'-ethylcarbodiimide hydrochloride (EDAC) and 47 mg (0.32 mmol) of 1-hydroxybenzotriazole (HOBT) in 2 ml of dimethylformamide. 95 mg of the expected product are obtained.

$^1$H NMR (DMSO D$_6$), δ (ppm): 10.25 (s, 1H); 8.5 (d, 2H); 8.35 (s, 1H); 7.85 (d, 1H); 7.75 (d, 1H); 7.6 (s, 1H); 7.45 (s, 1H); 7.3 (d, 1H); 7.0 (d, 2H); 6.4 (d, 1H); 5.95 (s, 2H); 3.9 (t, 4H); 2.3 (quint., 2H); 0.25 (s, 9H).

LC-MS: 456 ([M+H]+, Rt=0.95 min.).

EXAMPLE 17

Compound No. 17

N-[6-(Azetidin-1-yl)pyridin-3-yl]-5-triethylsilyl-1-[(3-fluorophenyl)methyl]-1H-indole-2-carboxamide 17.1 Ethyl 5-bromo-1-[(3-fluorophenyl)methyl]-1H-indole-2-carboxylate A solution of 5.0 g (18.65 mmol) of ethyl 5-bromo-1H-indole-2-carboxylate in 25 ml of dry DMF is added dropwise, at 0° C., to a suspension of 0.96 g (24.24 mmol) of sodium hydride (60%) in 15 ml of dry DMF, maintained under an inert atmosphere. The reaction mixture is stirred at ambient temperature for 1 hour. 4.23 g (2.75 mmol) of 3-fluorobenzyl bromide are subsequently added dropwise, at 0° C. The reaction mixture is then stirred for 18 h at ambient temperature and then diluted with 200 ml of a mixture of water and ethyl acetate (1/1). The resulting mixture is separated by settling out and the aqueous phase is extracted with 2×30 ml of ethyl acetate. The combined organic phases are washed three times with water, dried over sodium sulphate, filtered and concentrated under reduced pressure. The resulting oil is purified by silica gel column chromatography, elution being carried out with a mixture of heptane and ethyl acetate. 5.76 g of the expected product are isolated.

$^1$H NMR (DMSO D$_6$), δ (ppm): 8.0 (s, 1H); 7.6 (d, 1H); 7.45 (d, 1H); 7.35 (s, 1H); 7.3 (m, 1H); 7.05 (m, 1H); 6.85 (m, 2H); 5.9 (s, 2H); 4.3 (q, 2H); 1.3 (t, 3H).

LC-MS: 376 ([M+H]+, Rt=11.8).

17.2 5-Bromo-1-[(3-fluorophenyl)methyl]-1H-indole-2-carboxylic acid

A solution of 1.5 g (3.99 mmol) of ethyl 5-bromo-1-[(3-fluorophenyl)methyl]-1H-indole-2-carboxylate, obtained in stage 17.1, and 0.67 g (11.96 mmol) of potassium hydroxide, in 45 ml of a mixture (v/v/v) of methanol, dioxane and water, is stirred at reflux for three hours. After this period of time, the reaction mixture is concentrated under reduced pressure and then taken up in 10 ml of water. The medium is acidified at pH 1 by successive additions of 1N hydrochloric acid. The precipitate is recovered by filtration, washed with water and then dried under reduced pressure. 1.17 g of the expected product are thus isolated, which product is used as it is in the subsequent stage.

LC-MS: 346 ([M−H]−, Rt=3.37 min.).

17.3 N-[6-(Azetidin-1-yl)pyridin-3-yl]-5-bromo-1-[(3-fluorophenyl)methyl]-1H-indole-2-carboxamide 0.77 g (4.02 mmol) of N-(3-dimethylaminopropyl)-N'-ethylcarbodiimide hydrochloride (EDAC) and 0.54 g (4.02 mmol) of 1-hydroxybenzotriazole (HOBT) are added to a solution, stirred at 20° C. under an inert atmosphere, of 1.4 g (4.02 mmol) of 5-bromo-1-[(3-fluorophenyl)methyl]-1H-indole-2-carboxylic acid, prepared in stage 17.2, in 20 ml of DMF. The reaction mixture is stirred at ambient temperature for 20 minutes. 0.66 g (4.42 mmol) of 3-amino-6-(azetidin-1-yl)pyridine, prepared according to the protocol described in stage 1.6, is subsequently added to the reaction mixture. After stirring at 20° C. for 18 hours, the reaction mixture is poured into a mixture of 50 ml of water and 50 ml of ethyl acetate. The resulting mixture is separated by settling out and the aqueous phase is extracted with 20 ml of ethyl acetate. The combined organic phases are washed three times with 30 ml of water, dried over sodium sulphate and then concentrated under reduced pressure. The isolated product is subsequently precipitated, then washed with isopropyl ether at reflux, filtered under hot conditions, and then dried under reduced pressure. 11.46 g of the expected product are thus isolated.

$^1$H NMR (DMSO D$_6$), δ (ppm): 10.4 (s, 1H); 8.38 (d, 1H); 8.0 (d, 1H); 7.85 (dd, 1H); 7.6 (d, 1H); 7.45-7.25 (m, 3H); 7.05 (dt, 1H); 6.9 (m, 2H); 6.4 (d, 1H); 5.9 (s, 2H); 3.9 (t, 4H); 2.3 (quint., 2H).

LC-MS: 479 ([M+H]+, Rt=1.39 min.).

17.4 N-[6-(Azetidin-1-yl)pyridin-3-yl]-5-triethylsilyl-1-[(3-fluorophenyl)methyl]-1H-indole-2-carboxamide (Compound No. 17)

Compound No. 17 was prepared according to a process similar to that described in stage 8.4, by reacting 0.15 g (0.31 mmol) of N-[6-(azetidin-1-yl)pyridin-3-yl]-5-bromo-1-[(3-fluorophenyl)methyl]-1H-indole-2-carboxamide, prepared according to the protocol described in stage 17.3, with 110 mg (0.93 mmol) of triethylsilane in the presence of 0.2 g (0.94 mmol) of potassium triphosphate and of 16 mg (0.03 mmol) of bis(tri-tert-butylphosphine)palladium in 2 ml of dry 1-methyl-2-pyrrolidinone (NMP). 26 mg of the expected product are obtained.

Mp=166-168° C.

$^1$H NMR (DMSO D$_6$), δ (ppm): 10.2 (s, 1H); 8.4 (d, 1H); 7.85 (m, 2H); 7.55 (d, 1H); 7.35 (m, 3H); 7.05 (m, 1H); 6.95

(m, 2H); 6.4 (d, 1H); 5.9 (s, 2H); 3.9 (t, 4H); 2.3 (quint., 2H); 1.65 (m, 5H); 0.95 (m, 9H); 0.8 (m, 6H).

LC-MS: 515 ([M+H]+, Rt=1.55).

EXAMPLE 18

Compound No. 18

N-[6-(Azetidin-1-yl)pyridin-3-yl]-5-tert-butyl(dimethyl)silyl-1-[(3-fluorophenyl)methyl]-1H-indole-2-carboxamide Compound No. 18 was prepared according to a process similar to that described in stage 8.4, by reacting 0.15 g (0.31 mmol) of N-[6-(azetidin-1-yl)pyridin-3-yl]-5-bromo-1-[(3-fluorophenyl)methyl]-1H-indole-2-carboxamide, prepared according to the protocol described in stage 17.3, with 108 mg (0.93 mmol) of tert-butyldimethylsilane in the presence of 0.2 g (0.94 mmol) of potassium triphosphate and of 16 mg (0.03 mmol) of bis(tri-tert-butylphosphine)palladium in 2 ml of dry 1-methyl-2-pyrrolidinone (NMP). 28 mg of the expected product are obtained.

Mp=110-112° C.

$^1$H NMR (DMSO D$_6$), δ (ppm): 10.2 (s, 1H); 8.4 (d, 1H); 7.85 (m, 2H); 7.55 (d, 1H); 7.4-7.3 (m, 3H); 7.05 (m, 1H); 6.95 (m, 2H); 6.4 (d, 1H); 5.9 (s, 2H); 3.9 (t, 4H); 2.3 (quint., 2H); 0.9 (s, 9H); 0.3 (s, 6H).

LC-MS: 515 ([M+H]+, Rt=1.53).

EXAMPLE 19

Compound No. 19

N-[6-(Pyrrolidin-1-yl)pyridin-3-yl]-5-(cyclohexyl)dimethylsilyl-1-[(3-fluorophenyl)methyl]-1H-indole-2-carboxamide 19.1 N-[6-(Pyrrolidin-1-yl)pyridin-3-yl]-5-iodo-1-[(3-fluorophenyl)methyl]-1H-indole-2-carboxamide The compound was prepared according to a process similar to that described in stage 5.4, by reacting 0.3 g (0.76 mmol) of 5-iodo-1-[(3-fluorophenyl)methyl]-1H-indole-2-carboxylic acid, prepared according to the protocol described in stage 8.2, with 148 mg (0.91 mmol) of 3-amino-6-(pyrrolidin-1-yl)pyridine in the presence of 145 mg (0.76 mmol) of N-(3-dimethylaminopropyl)-N'-ethylcarbodiimide hydrochloride (EDAC) and of 105 mg (0.76 mmol) of 1-hydroxybenzotriazole (HOBT) in 5 ml of dimethylformamide. 290 mg of the expected product are obtained.

$^1$H NMR (DMSO D$_6$), δ (ppm): 10.3 (s, 1H); 8.4 (d, 1H); 8.15 (s, 1H); 7.85 (dd, 1H); 7.55 (d, 1H); 7.45 (d, 1H); 7.3 (m, 2H); 7.05 (m, 1H); 6.95 (m, 2H); 6.45 (d, 1H); 5.9 (s, 2H); 3.4 (m, 4H); 1.9 (m, 4H).

LC-MS: 541 ([M+H]+, Rt=1.25).

19.2 N-[6-(Pyrrolidin-1-yl)pyridin-3-yl]-5-(cyclohexyl)dimethylsilyl-1-[(3-fluorophenyl)methyl]-1H-indole-2-carboxamide (Compound 19)

Compound No. 19 was prepared according to a process similar to that described in stage 8.4, by reacting 0.15 g (0.28 mmol) of N-[6-(pyrrolidin-1-yl)pyridin-3-yl]-5-iodo-1-[(3-fluorophenyl)methyl]-1H-indole-2-carboxamide, prepared according to the protocol described in stage 19.1, with 120 mg (0.83 mmol) of cyclohexyldimethylsilane in the presence of 0.18 g (0.83 mmol) of potassium triphosphate and of 14 mg (0.027 mmol) of bis(tri-tert-butylphosphine)palladium in 2 ml of dry 1-methyl-2-pyrrolidinone (NMP). 41 mg of the expected product are obtained.

Mp=192-194° C.

$^1$H NMR (DMSO D$_6$), δ (ppm): 10.2 (s, 1H); 8.4 (d, 1H); 7.85 (m, 2H); 7.55 (d, 1H); 7.4-7.3 (m, 3H); 7.05 (m, 1H); 6.95 (m, 2H); 6.45 (d, 1H); 5.9 (s, 2H); 3.4 (m, 4H); 2.0 (m, 4H); 1.7 (m, 4H); 1.15 (m, 6H); 0.8 (m, 1H); 0.3 (s, 6H).

LC-MS: 555 ([M+H]+, Rt=1.64).

EXAMPLE 20

Compound No. 20

N-[6-(Azetidin-1-yl)pyridin-3-yl]-5-(phenyl)dimethylsilyl-1-[(3-fluorophenyl)methyl]-1H-indole-2-carboxamide (Compound No. 20)

Compound No. 20 was prepared according to a process similar to that described in stage 8.4, by reacting 0.25 g (0.28 mmol) of N-[6-(azetidin-1-yl)pyridin-3-yl]-5-iodo-1-[(3-fluorophenyl)methyl]-1H-indole-2-carboxamide, prepared according to the protocol described in stage 8.3, with 71 mg (0.52 mmol) of phenyldimethylsilane in the presence of 0.30 g (1.42 mmol) of potassium triphosphate and of 24 mg (0.05 mmol) of bis(tri-tert-butylphosphine)palladium in 3 ml of dry 1-methyl-2-pyrrolidinone (NMP). 140 mg of the expected product are obtained in the form of a white solid. Mp=200-202° C.

$^1$H NMR (DMSO D$_6$), δ (ppm): 10.2 (s, 1H); 8.4 (s, 1H); 7.85 (m, 2H); 7.55 (m, 3H); 7.45-7.25 (m, 6H); 7.05 (m, 1H); 6.95 (m, 2H); 6.4 (d, 1H); 5.9 (s, 2H); 3.95 (t, 4H); 2.3 (quint., 2H); 0.6 (s, 6H).

LC-MS: 535 ([M+H]+, Rt=1.44).

EXAMPLE 21

Compound No. 21

N-[6-(Azetidin-1-yl)pyridin-3-yl]-5-(isopropyl)dimethylsilyl-1-[(3-fluorophenyl)methyl]-1H-indole-2-carboxamide Compound No. 21 was prepared according to a process similar to that described in stage 8.4, by reacting 0.15 g (0.31 mmol) of N-[6-(azetidin-1-yl)pyridin-3-yl]-5-bromo-1-[(3-fluorophenyl)methyl]-1H-indole-2-carboxamide, prepared according to the protocol described in stage 17.3, with 95 mg (0.93 mmol) of dimethyl(isopropyl)silane in the presence of 0.2 g (0.94 mmol) of potassium triphosphate and of 16 mg (0.03 mmol) of bis(tri-tert-butylphosphine)palladium in 2 ml of dry 1-methyl-2-pyrrolidinone (NMP). 23 mg of the expected product are obtained.

Mp=179-180° C.

$^1$H NMR (DMSO D$_6$), δ (ppm): 10.25 (s, 1H); 8.35 (s, 1H); 7.85 (m, 2H); 7.55 (m, 1H); 7.3 (m, 3H); 7.05 (m, 1H); 6.95 (m, 2H); 6.4 (d, 1H); 5.9 (s, 2H); 3.9 (m, 4H); 2.3 (m, 2H); 0.9 (m, 7H); 0.3 (s, 6H).

LC-MS: 501 ([M+H]+, Rt=1.49).

EXAMPLE 22

Compound No. 22

N-[6-(Azetidin-1-yl)pyridin-3-yl]-5-(methyl)diethyl-silyl-1-[(3-fluorophenyl)methyl]-1H-indole-2-carboxamide Compound No. 22 was prepared according to a process similar to that described in stage 8.4, by reacting 0.15 g (0.31 mmol) of N-[6-(azetidin-1-yl)pyridin-3-yl]-5-bromo-1-[(3-fluorophenyl)methyl]-1H-indole-2-carboxamide, prepared according to the protocol described in stage 17.3, with 95 mg (0.93 mmol) of diethyl(methyl)silane in the presence of 0.2 g (0.94 mmol) of potassium triphosphate and of 16 mg (0.03 mmol) of bis(tri-tert-butylphosphine)palladium in 2 ml of dry 1-methyl-2-pyrrolidinone (NMP). 13 mg of the expected product are obtained.

Mp=171-173° C.

$^1$H NMR (DMSO D$_6$), δ (ppm): 10.2 (s, 1H); 8.35 (s, 1H); 7.85 (m, 2H); 7.55 (m, 1H); 7.35 (m, 3H); 7.05 (m, 1H); 6.95 (m, 2H); 6.4 (d, 1H); 5.9 (s, 2H); 3.9 (m, 4H); 2.3 (m, 2H); 0.95 (m, 6H); 0.8 (m, 4H); 0.25 (s, 3H).

LC-MS: 501 ([M+H]+, Rt=1.50).

Table 1 which follows illustrates the chemical structures and the physical properties of some compounds of general formula (I) according to the invention.

In this table:
- the compounds of general formula (I) are defined with n equal to 1;
- the column "Mp (° C.) or [MH]$^+$" gives, respectively, either the melting points of the products in degrees Celsius (° C.), or their mass peak in LC-MS; the liquid chromatography (LC) method used to determine the mass peaks of compounds No. 15 and 16 of Table 1 is the following:

Apparatus: HPLC/TOF

Mobile phases: A=H$_2$O+0.05% TFA and B=ACN+0.035% TFA

Gradient 3 min: T0: 98% A T1.6 to T2.1 min: 100% B T2.5 to T3 min: 98% A

Flow rate: 1.0 ml/min–T° column=40° C.—Injection 2 μL

Column Acquity BEH C18 (50×2.1 mm; 1.7 μm)

- the compounds are in the form of a free base;
- "CH$_3$" corresponds to a methyl group, "Et" corresponds to an ethyl group, "cHex" corresponds to a cyclohexyl group, "tertBu" corresponds to a tert-butyl group, "Ph" corresponds to a phenyl group, "iPr" corresponds to an isopropyl group.

TABLE 1

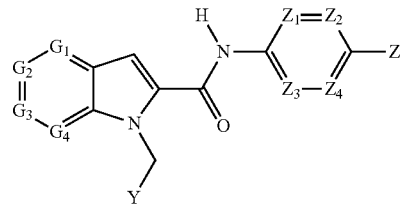

| No | G$_1$, G$_2$, G$_3$, G$_4$ | Y | Z$_1$, Z$_2$, Z$_3$, Z$_4$ | Z | Mp (° C.) (or [MH]$^+$) |
|---|---|---|---|---|---|
| 1 | CH, CH, —Si(CH$_3$)$_3$, CH | 3-fluorophenyl | CH, CH, CH, N | Azetidinyl | 208-210 |
| 2 | CH, CH, —Si(CH$_3$)$_3$, CH | 3-fluorophenyl | CH, CH, CH, N | 3-Hydroxy-azetidinyl | 188-189 |
| 3 | CH, —Si(CH$_3$)$_3$, CH, CH | 3-fluorophenyl | CH, CH, CH, N | azetidinyl | 221-213 |
| 4 | CH, —Si(CH$_3$)$_3$, CH, CH | 3-fluorophenyl | CH, CH, CH, N | 3-Hydroxy-azetidinyl | 207-208 |
| 5 | CH, CH, CH, —Si(CH$_3$)$_3$ | 3-fluorophenyl | CH, CH, CH, N | Azetidinyl | 160-162 |
| 6 | CH, CH, CH, —Si(CH$_3$)$_3$ | 3-fluorophenyl | CH, CH, CH, N | 3-Hydroxy-azetidinyl | 215-217 |
| 7 | CH, —Si(CH$_3$)$_3$, CH, CH | 3-fluorophenyl | CH, CH, CH, N | Dimethyl-amino | 204-205 |
| 8 | CH, —Si(Me$_2$)Et, CH, CH | 3-fluorophenyl | CH, CH, CH, N | Azetidinyl | 188-189 |
| 9 | CH, —Si(cHex)(Me$_2$), CH, CH | 3-fluorophenyl | CH, CH, CH, N | Azetidinyl | 202-203 |
| 10 | CH, CH, —Si(CH$_3$)$_3$, CH | 3-(trifluoromethyl)-phenyl | CH, CH, CH, N | Azetidinyl | 167-168 |
| 11 | CH, CH, —Si(CH$_3$)$_3$, CH | 3-(trifluoromethyl)-phenyl | CH, CH, CH, N | 3-Hydroxy-azetidinyl | 183-184 |
| 12 | CH, —SiCH$_3$(Ph)$_2$, CH, CH | 3-fluorophenyl | CH, CH, CH, N | Azetidinyl | 98-100 |
| 13 | CH, —Si(CH$_3$)$_3$, CH, CH | 3-(trifluoromethyl)-phenyl | CH, CH, CH, N | Azetidinyl | 199-200 |
| 14 | CH, —Si(CH$_3$)$_3$, CH, CH | 3-(trifluoromethyl)-phenyl | CH, CH, CH, N | 3-Hydroxy-azetidinyl | 217-218 |
| 15 | CH, CH, —Si(CH$_3$)$_3$, CH | pyridin-4-yl | CH, CH, CH, N | 3-Hydroxy-azetidinyl | (472) |
| 16 | CH, CH, —Si(CH$_3$)$_3$, CH | pyridin-4-yl | CH, CH, CH, N | Azetidinyl | (456) |
| 17 | CH, —Si(Et)$_3$, CH, CH | 3-fluorophenyl | CH, CH, CH, N | Azetidinyl | 166-168 |
| 18 | CH, —Si(tertBu)(Me$_2$), CH, CH | 3-fluorophenyl | CH, CH, CH, N | Azetidinyl | 110-112 |
| 19 | CH, —Si(cHex)(Me$_2$), CH, CH | 3-fluorophenyl | CH, CH, CH, N | Pyrrolidinyl | 192-194 |
| 20 | CH, —Si(Me$_2$)Ph, CH, CH | 3-fluorophenyl | CH, CH, CH, N | Azetidinyl | 200-202 |
| 21 | CH, —Si(iPr)(Me$_2$), CH, CH | 3-fluorophenyl | CH, CH, CH, N | Azetidinyl | 179-180 |
| 22 | CH, —Si(Et$_2$)(Me), CH, CH | 3-fluorophenyl | CH, CH, CH, N | Azetidinyl | 171-173 |

The compounds of the invention were subjected to in vitro and in vivo pharmacological tests which demonstrated their value as substances with therapeutic activities.

The compounds of the invention also have water-solubility characteristics which promote good activity in vivo.

Test for Inhibition of the Current Induced by Capsaicin on Rat DRGs

Primary Culture of Rat Dorsal Route Ganglion (DRG) Cells:

The neurones of the DRG naturally express the TRPV1 receptor.

Newborn rat DRG primary cultures are prepared from 1-day-old rat pups. Briefly, after dissection, the ganglia are trypsinized and the cells are mechanically dissociated by controlled trituration. The cells are resuspended in an Eagle's basal culture medium containing 10% of foetal calf serum, 25 mM KCl, 2 mM glutamine, 100 µg/ml gentamicin and 50 ng/ml of NGF, and then deposited onto laminin-coated glass coverslips ($0.2\times10^6$ cells per coverslip) which are then placed in Corning 12-well dishes. The cells are incubated at 37° C. in a humidified atmosphere containing 5% $CO_2$ and 95% air. Cytosine β-D-arabinoside (1 µM) is added 48 h after placing in culture, in order to prevent the development of non-neuronal cells. The coverslips are transferred into the experimental chambers for the patch-clamp studies after 7-10 days of culture.

Electrophysiology:

The measuring chambers (volume 800 µl) containing the cell preparation are placed on the platform of an inverted microscope (Olympus IMT2) equipped with Hoffman optics (Modulation Contrast, New York) and observed at the magnification of ×400. The chambers are continually perfused by gravity (2.5 ml/min) by means of a solution distributing device with 8 inlets, and the sole outlet of which, constituted by a polyethylene tube (500 µm aperture), is placed at least 3 mm from the cell studied. The "whole cell" configuration of the patch-clamp technique was used. The borosilicate glass pipettes (resistance 5-10 MOhms) are moved close to the cell by means of a 3D piezoelectric micromanipulator (Burleigh, PC1000). The overall currents (membrane potential fixed at −60 mV) are recorded with an Axopatch 1D amplifier (Axon Instruments, Foster city, Calif.), connected to a PC controlled by Pclamp8 software (Axon Instruments). The current traces are recorded on paper and simultaneously digitized (sampling frequency 15 to 25 Hz) and acquired on the hard drive of the PC. The application of a micromolar solution of capsaicin causes, on the DRG cells (voltage fixed at −70 mV), an inward cationic current. In order to minimize the desensitization of the receptors, a minimum period of one minute is observed between two applications of capsaicin. After a control period (stabilization of the capsaicin response alone), the test compounds are applied alone at a given concentration (concentration of 10 nM or of 0.1 nM) for a period of 4 to 5 minutes, during which several capsaicin+compound tests are carried out (obtaining of maximum inhibition). The results are expressed as % inhibition of the control capsaicin response.

The percentages of inhibition of the capsaicin response (1 microM) are between 20% and 100% for the most active compounds of the invention tested at concentrations of 10 nM to 0.1 nM (see example in Table 2).

The compounds of the invention are therefore effective antagonists, in vitro, of TRPV1-type receptors.

TABLE 2

| Compound No. | % inhibition in DRG patch |
|---|---|
| 2 | 84% (1 nM) |
| 3 | 95% (10 nM) |

The results of these tests show that the most active compounds of the invention block the effects induced by stimulation of the TRPV1 receptors.

The compounds of the invention can therefore be used for the preparation of medicaments, in particular for the preparation of a medicament for preventing or treating pathologies in which TRPV1-type receptors are involved.

Thus, according to another of its aspects, a subject of the invention is medicaments which comprise a compound of formula (I), or a pharmaceutically acceptable salt, or else a hydrate or a solvate of said compound.

These medicaments can be used in therapeutics, in particular in the prevention and/or treatment of pain and inflammation, chronic pain, neuropathic pain (trauma-related, diabetic, metabolic, infection-related or toxic pain, or pain induced by an anticancer or iatrogenic treatment), (osteo-)arthritic pain, rheumatic pain, fibromyalgia, back pain, cancer-related pain, facial neuralgia, headaches, migraine, dental pain, burns, sunburn, animal bites or insect bites, post-herpetic neuralgia, muscle pain, a trapped nerve (central and/or peripheral), spinal column and/or brain trauma, ischaemia (of the spinal cord and/or of the brain), neurodegeneration, haemorrhagic strokes (of the spinal cord and/or of the brain) and post-stroke pain.

The compounds of the invention can be used for the preparation of a medicament for preventing and/or treating urological disorders such as bladder hyperactivity, bladder hyperreflexia, bladder instability, incontinence, urgent urination, urinary incontinence, cystitis, nephretic colic, pelvic hypersensitivity and pelvic pain.

The compounds of the invention can be used for the preparation of a medicament for preventing and/or treating gynaecological disorders such as vulvodynia, pain associated with salpingitis or with dysmenorrhoea.

These products can also be used for the preparation of a medicament for preventing and/or treating gastrointestinal disorders such as gastro-oesophageal reflux disorder, stomach ulcers, duodenal ulcers, functional dyspepsia, colitis, IBS, Crohn's disease, pancreatitis, oesophagitis or biliary colic.

The compounds of the invention can also be used for the preparation of a medicament for preventing and/or treating metabolic disorders such as diabetes.

Similarly, the products of the invention can be used in the prevention and/or treatment of respiratory disorders such as asthma, coughing, COPD, bronchoconstriction and inflammatory disorders. These products can also be used for preventing and/or treating psoriasis, pruritus, dermal, ocular or mucosal irritations, herpes and shingles.

The compounds of the invention can also be used for the preparation of a medicament for treating depression.

The compounds of the invention could also be used for treating central nervous system diseases such as multiple sclerosis.

The compounds of the invention could also be used for treating cancers.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or a solvate of said compound, and also at least one pharmaceutically acceptable excipient.

Said excipients are selected, according to the pharmaceutical form and the method of administration desired, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its optional salt, solvate or hydrate, can be administered in unit administration form, as a mixture with conventional pharmaceutical excipients, to animals and to humans for the prophylaxis or treatment of the disorders or diseases mentioned above.

The appropriate unit administration forms include oral forms such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

Said unit forms contain a dose so as to allow a daily administration of from 0.001 to 30 mg of active ingredient per kg of body weight, according to the galenical form.

There may be specific cases where higher or lower dosages are appropriate; such dosages do not depart from the scope of the invention. According to the usual practice, the dosage appropriate for each patient is determined by the physician according to the method of administration and the weight and response of said patient.

According to another of its aspects, the present invention also relates to a method for treating the pathologies indicated above, which comprises the administration, to a patient, of an effective dose of a compound according to the invention, or a pharmaceutically acceptable salt, a hydrate or a solvate thereof.

What is claimed is:
1. A compound corresponding to formula (I):

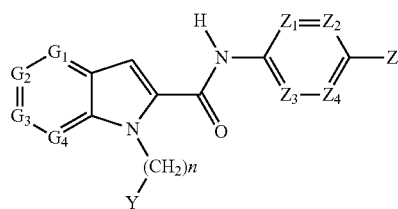

wherein:
$G_1$, $G_2$, $G_3$ and $G_4$ are, independently of one another, a C—X group or a nitrogen atom;

X is chosen from a hydrogen atom, a halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, $NR_1R_2$, aryl-$C_1$-$C_6$-alkylene-O, aryl, heteroaryl or —Si($X_1$)($X_2$)($X_3$) group; the $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkoxyl and $C_3$-$C_7$-cycloalkyl-$C_1$-$C_6$-alkylene-O— groups being optionally substituted with a hydroxyl, $C_1$-$C_6$-alkoxyl or $NR_4R_5$ group; the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

one of $G_1$, $G_2$, $G_3$ and $G_4$ and at most one of $G_1$, $G_2$, $G_3$ and $G_4$ is a C—X group where X is an —Si($X_1$)($X_2$)($X_3$) group;

$X_1$, $X_2$ and $X_3$ are, independently of one another, a $C_1$-$C_6$-alkyl, $C_3$-$C_7$-cycloalkyl, $C_3$-$C_7$-cycloalkyl-$C_1$-$C_6$-alkyl, hydroxyl, aryl or heteroaryl group;

the aryl or heteroaryl groups of $X_1$, $X_2$, $X_3$ being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

the $C_1$-$C_6$-alkyl, $C_3$-$C_7$-cycloalkyl and $C_3$-$C_7$-cycloalkyl-$C_1$-$C_6$-alkyl groups of $X_1$, $X_2$, $X_3$ being optionally substituted with one or more substituents chosen from a hydroxyl, $C_1$-$C_6$-alkoxyl, aryl-O—, $NR_1R_2$, aryl or heteroaryl group; the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

it also being possible for $X_1$ and $X_2$ to form, together with the silicon atom which bears them, a 4- to 7-membered ring optionally containing a heteroatom chosen from O, S and N;

n is equal to 0, 1, 2 or 3;

Y is an aryl or a heteroaryl; the aryl or the heteroaryl being optionally substituted with one or more substituents chosen from a halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, thiol, —S(O)—$C_1$-$C_6$-alkyl, —S(O)$_2$—$C_1$-$C_6$-alkyl, C(O)$NR_1R_2$, $SO_2NR_1R_2$, $SF_5$, nitro, $OCONR_1R_2$, $NR_3COR_4$, $NR_3CONR_1R_2$, $NR_1R_2$, $NR_3SO_2NR_1R_2$, $NR_3COR_4$, $NR_3SO_2R_5$, aryl-$C_1$-$C_6$-alkylene or aryl group; the aryl and the aryl-$C_1$-$C_6$-alkylene being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$Z_1$, $Z_2$, $Z_3$, and $Z_4$ are, independently of one another, a nitrogen atom or a $C(R_6)$ group, at least one corresponding to a nitrogen atom and at least one corresponding to a $C(R_6)$ group; the nitrogen atom or one of the nitrogen atoms present in the ring, defined as nitrogen of position 1, being optionally substituted with $R_7$ when the carbon atom at position 2 or 4 relative to this reference nitrogen is substituted with an oxo or thio group;

Z is
either a cyclic amine linked via the nitrogen atom, of formula:

in which:
A is a $C_1$-$C_7$-alkylene group optionally substituted with one or two $R_8$ groups;
B is a $C_1$-$C_7$-alkylene group optionally substituted with one or two $R_9$ groups;
L is a bond, or a sulphur, oxygen or nitrogen atom; the nitrogen atom being optionally substituted with an $R_{10}$ or $R_{11}$;
the carbon atoms of the cyclic amine Z being optionally substituted with one or more $R_{12}$ groups which may be identical to or different from one another;
or an acyclic amine, linked via the nitrogen atom, of formula NRaRb in which Ra and Rb are, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-alkyl-C(O)—, HO—C(O)—$C_1$-$C_6$-alkylene, $C_1$-$C_6$-alkyl-O—C(O)—$C_1$-$C_6$-alkylene, aryl or heteroaryl group, it being possible for Ra and Rb to be optionally substituted with one or more Rc groups which may be identical to or different from one another;
Rc is a halogen atom, or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, cyano, C(O)NR$_1$R$_2$, NR$_1$R$_2$, SO$_2$NR$_1$R$_2$, NR$_3$COR$_4$, NR$_3$SO$_2$R$_5$, OC(O)NR$_1$R$_2$, NR$_3$COOR$_5$, NR$_3$CONR$_1$R$_2$, NR$_3$SO$_2$NR$_1$R$_2$, hydroxyl, thiol, oxo, thio, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
$R_1$ and $R_2$ are, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group; or $R_1$ and $R_2$ form, together with the nitrogen atom which bears them, an azetidinyl, pyrrolidinyl, piperidinyl, azepinyl, morpholinyl, thiomorpholinyl, piperazinyl or homopiperazinyl group, this group being optionally substituted with a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
$R_3$ and $R_4$ are, independently of one another,
a hydrogen atom or a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
or $R_3$ and $R_4$ together form a ($C_2$-$C_5$)alkylene group;
or $R_1$ and $R_3$ together form a ($C_2$-$C_5$)alkylene group;
$R_5$ is a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
or $R_3$ and $R_5$ together form a ($C_2$-$C_5$)alkylene group;
$R_6$ is a hydrogen or halogen atom, or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, hydroxyl, thiol, oxo, thio, aryl, aryl-$C_1$-$C_6$-alkylene or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
$R_7$ is a hydrogen atom, or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, aryl, aryl-$C_1$-$C_6$-alkylene or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
$R_8$, $R_9$ and $R_{10}$ are defined such that:
two $R_8$ groups may together form a bond or a $C_1$-$C_6$-alkylene group;
two $R_9$ groups may together form a bond or a $C_1$-$C_6$-alkylene group;
$R_8$ and $R_9$ may together form a bond or a $C_1$-$C_6$-alkylene group;
$R_8$ and $R_{10}$ may together form a bond or a $C_1$-$C_6$-alkylene group;
$R_9$ and $R_{10}$ may together form a bond or a $C_1$-$C_6$-alkylene group;
$R_{11}$ is a hydrogen atom, or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, hydroxyl, $C_1$-$C_6$-alkyl-CO—, COOR$_5$, C(O)NR$_1$R$_2$, aryl-$C_1$-$C_6$-alkylene, aryl or heteroaryl group, the aryl and the heteroaryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group;

$R_{12}$ is a fluorine atom, a $C_1$-$C_6$-alkyl group optionally substituted with an $R_{13}$ group; $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-cycloalk-1,1-diyl, $C_3$-$C_7$-heterocycloalk-1,1-diyl optionally substituted on a nitrogen atom with an $R_{11}$ group; $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, $CO_2H$, $C(O)O$—$C_1$-$C_6$-alkyl, $C(O)NR_1R_2$, $NR_1R_2$, $NR_3COR_4$, $OC(O)NR_1R_2$, $NR_3COOR_5$, $NR_3CONR_1R_2$, hydroxyl, thiol, oxo, thio, aryl-$C_1$-$C_6$-alkylene or aryl; the aryl being optionally substituted with one or more substituents chosen from a halogen, and a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group; and $R_{13}$ is a $C_1$-$C_6$-alkoxyl, $C_3$-$C_7$-cycloalkoxyl, $C_3$-$C_7$-cycloalkyl-$C_1$-$C_6$-alkylene-O—, $C(O)NR_1R_2$, $NR_1R_2$, $NR_3COR_4$, $OC(O)NR_1R_2$, $NR_3COOR_5$ or hydroxyl group;

it being possible for the nitrogen atom(s) of the compounds of formula (I) to be in oxidized form;

or an acid addition salt thereof.

2. The compound of formula (I) according to claim 1, wherein:

one of $G_1$, $G_2$, $G_3$ and $G_4$ is a C—X group where X is an —$Si(X_1)(X_2)(X_3)$ group; the others of $G_1$, $G_2$, $G_3$ and $G_4$ being a CH group; and $X_1$, $X_2$ and $X_3$ are, independently of one another, a $C_1$-$C_6$-alkyl, $C_3$-$C_7$-cycloalkyl or aryl group;

or an acid addition salt thereof.

3. The compound of formula (I) according to claim 1, wherein n is equal to 1; or an acid addition salt thereof.

4. The compound of formula (I) according to claim 1, wherein Y is an aryl or a heteroaryl; the aryl or the heteroaryl being optionally substituted with one or more groups chosen from a halogen atom and a $C_1$-$C_6$-fluoroalkyl group;

or an acid addition salt thereof.

5. The compound of formula (I) according to claim 1, wherein $Z_1$, $Z_2$, $Z_3$ and $Z_4$ are, independently of one another, a nitrogen atom or a $C(R_6)$ group, one corresponding to a nitrogen atom and the others corresponding to a $C(R_6)$ group; and $R_6$ is a hydrogen atom;

or an acid addition salt thereof.

6. The compound of formula (I) according to claim 1, wherein:

Z is a cyclic amine linked via the nitrogen atom, of formula:

in which:
A is a $C_1$-$C_7$-alkylene group optionally substituted with one or two $R_8$ groups;
B is a $C_1$-$C_7$-alkylene group optionally substituted with one or two $R_9$ groups;
L is a bond, or a sulphur, oxygen or nitrogen atom; the nitrogen atom being optionally substituted with an $R_{10}$ or $R_{11}$ group;
the carbon atoms of the cyclic amine Z being optionally substituted with one or more $R_{12}$ groups which may be identical to or different from one another;
$R_8$, $R_9$, $R_{10}$, $R_{11}$ and $R_{12}$ are as defined in formula (I) according to claim 1;
or an acid addition salt thereof.

7. The compound of formula (I) according to claim 1, wherein:

Z is a cyclic amine linked via the nitrogen atom, of formula:

in which:
A is a $C_1$-$C_3$-alkylene group;
B is a $C_1$-$C_3$-alkylene group;
L is a bond;
the carbon atoms of the cyclic amine Z being optionally substituted with one or more $R_{12}$ groups which may be identical to or different from one another; and
$R_{12}$ is a hydroxyl group;
or an acid addition salt thereof.

8. The compound of formula (I) according to claim 1, wherein Z is an acyclic amine, linked via the nitrogen atom, of formula NRaRb in which Ra and Rb are, independently of one another, a hydrogen atom or a $C_1$-$C_6$-alkyl group;

or an acid addition salt thereof.

9. The compound of formula (I) according to claim 1, wherein:

one of $G_1$, $G_2$, $G_3$ and $G_4$ is a C—X group where X is an —$Si(X_1)(X_2)(X_3)$ group; the others of $G_1$, $G_2$, $G_3$ and $G_4$ being a CH group;

$X_1$, $X_2$ and $X_3$ are, independently of one another, a $C_1$-$C_6$-alkyl, $C_3$-$C_7$-cycloalkyl or aryl group;

n is equal to 1;

Y is an aryl or a heteroaryl; the aryl or the heteroaryl being optionally substituted with one or more groups chosen from a halogen atom or a $C_1$-$C_6$-fluoroalkyl group;

$Z_1$, $Z_2$, $Z_3$ and $Z_4$ are, independently of one another, a nitrogen atom or a $C(R_6)$ group, one corresponding to a nitrogen atom and the others corresponding to a $C(R_6)$ group; $R_6$ is a hydrogen atom;

Z is:

either a cyclic amine linked via the nitrogen atom, of formula:

in which:
A is a $C_1$-$C_3$-alkylene group;
B is a $C_1$-$C_3$-alkylene group;
L is a bond;
the carbon atoms of the cyclic amine Z being optionally substituted with one or more $R_{12}$ groups which may be identical to or different from one another;
$R_{12}$ is a hydroxyl group;
or an acyclic amine, linked via the nitrogen atom, of formula NRaRb in which Ra and Rb are, independently of one another, a hydrogen atom or a $C_1$-$C_6$-alkyl group;
or an acid addition salt thereof.

10. The compound of formula (I) according to claim 1, selected from the group consisting of:

N-[6-(azetidin-1-yl)pyridin-3-yl]-6-trimethylsilyl-1-[(3-fluorophenyl)methyl]-1H-indole-2-carboxamide;

N-[6-(3-hydroxyazetidin-1-yl)pyridin-3-yl]-6-trimethylsilyl-1-[(3-fluorophenyl)methyl]-1H-indole-2-carboxamide;

N-[6-(azetidin-1-yl)pyridin-3-yl]-5-trimethylsilyl-1-[(3-fluorophenyl)methyl]-1H-indole-2-carboxamide;

N-[6-(3-hydroxyazetidin-1-yl)pyridin-3-yl]-5-trimethylsilyl-1-[(3-fluorophenyl)methyl]-1H-indole-2-carboxamide;

N-[6-(azetidin-1-yl)pyridin-3-yl]-7-trimethylsilyl-1-[(3-fluorophenyl)methyl]-1H-indole-2-carboxamide;

N-[6-(3-hydroxyazetidin-1-yl)pyridin-3-yl]-7-trimethylsilyl-1-[(3-fluorophenyl)methyl]-1H-indole-2-carboxamide;

N-[6-(Dimethylamino)pyridin-3-yl]-5-trimethylsilyl-1-[(3-fluorophenyl)methyl]-1H-indole-2-carboxamide;

N-[6-(azetidin-1-yl)pyridin-3-yl]-5-(ethyl)dimethylsilyl-1-[(3-fluorophenyl)methyl]-1H-indole-2-carboxamide;

N-[6-(azetidin-1-yl)pyridin-3-yl]-5-(cyclohexyl)dimethylsilyl-1-[(3-fluorophenyl)methyl]-1H-indole-2-carboxamide;

1N-[6-(azetidin-1-yl)pyridin-3-yl]-6-trimethylsilyl-1-[[(3-trifluoromethyl)phenyl]methyl]-1H-indole-2-carboxamide;

N-[6-(3-hydroxyazetidin-1-yl)pyridin-3-yl]-6-trimethylsilyl-1-[[(3-trifluoromethyl)phenyl]methyl]-1H-indole-2-carboxamide;

N-[6-(azetidin-1-yl)pyridin-3-yl]-5-(diphenyl)methylsilyl-1-[(3-fluorophenyl)methyl]-1H-indole-2-carboxamide;

N-[6-(azetidin-1-yl)pyridin-3-yl]-5-trimethylsilyl-1-[[(3-trifluoromethyl)phenyl]methyl]-1H-indole-2-carboxamide;

N-[6-(3-hydroxyazetidin-1-yl)pyridin-3-yl]-5-trimethylsilyl-1-[[(3-trifluoromethyl)phenyl]methyl]-1H-indole-2-carboxamide;

N-[6-(3-hydroxyazetidin-1-yl)pyridin-3-yl]-6-trimethylsilyl-1-[(pyridin-4-yl)methyl]-1H-indole-2-carboxamide;

N-[6-(azetidin-1-yl)pyridin-3-yl)pyridin-3-yl]-6-trimethylsilyl-1-[(pyridin-4-yl)methyl]-1H-indole-2-carboxamide;

N-[6-(azetidin-1-yl)pyridin-3-yl]-5-triethylsilyl-1-[(3-fluorophenyl)methyl]-1H-indole-2-carboxamide;

N-[6-(azetidin-1-yl)pyridin-3-yl]-5-tert-butyl(dimethyl)silyl-1-[(3-fluorophenyl)methyl]-1H-indole-2-carboxamide;

N-[6-(Pyrrolidin-1-yl)pyridin-3-yl]-5-(cyclohexyl)dimethylsilyl-1-[(3-fluorophenyl)methyl]-1H-indole-2-carboxamide;

N-[6-(azetidin-1-yl)pyridin-3-yl]-5-phenyldimethylsilyl-1-[(3-fluorophenyl)methyl]-1H-indole-2-carboxamide;

N-[6-(azetidin-1-yl)pyridin-3-yl]-5-(isopropyl)dimethylsilyl-1-[(3-fluorophenyl)methyl]-1H-indole-2-carboxamide; and N-[6-(Azetidin-1-yl)pyridin-3-yl]-5-(methyl)diethylsilyl-1-[(3-fluorophenyl)methyl]-1H-indole-2-carboxamide; or an acid addition salt thereof.

11. A process for preparing a compound of formula (I) according to claim 1, comprising reacting a compound of formula (IV):

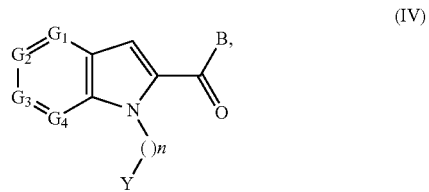

in which $G_1$, $G_2$, $G_3$ and $G_4$, Y and n are as defined in formula (I) according to claim 1 and B is a chlorine atom, with an amine of formula (V):

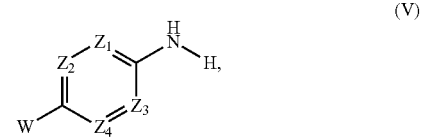

in which W=Z and Z, $Z_1$, $Z_2$, $Z_3$ and $Z_4$ are as defined in formula (I) according to claim 1, in a solvent.

12. A process for preparing a compound of formula (I) according to claim 1, comprising reacting a compound of formula (IV):

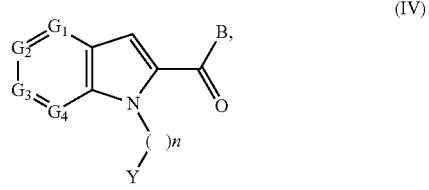

in which $G_1$, $G_2$, $G_3$ and $G_4$, Y and n are as defined in formula (I) according to claim 1 and B is a hydroxyl group, with an amine of formula (V):

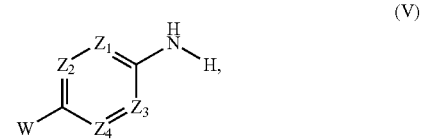

in which W=Z and Z, $Z_1$, $Z_2$, $Z_3$ and $Z_4$ are as defined in formula (I) according to claim 1, in the presence of a coupling agent, and optionally of a base, in a solvent.

13. A process for preparing a compound of formula (I) according to claim 1, comprising reacting a compound of formula (VI):

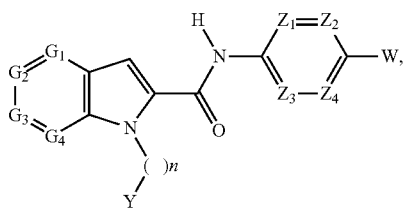

(VI)

in which $G_1$, $G_2$, $G_3$ and $G_4$, Y, n, $Z_1$, $Z_2$, $Z_3$ and $Z_4$ are as defined in formula (I) according to claim 1 and W is a halogen atom, with an amine of formula Z-H, in which Z is as defined in formula (I) according to claim 1.

14. A process for preparing a compound of formula (I) according to claim 1, comprising reacting a compound of formula (X):

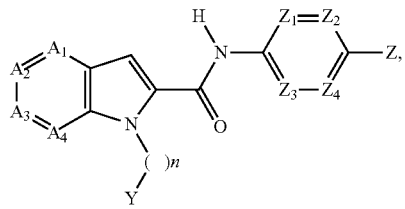

(X)

in which Y, n, Z, $Z_1$, $Z_2$, $Z_3$ and $Z_4$ are as defined in formula (I) according to claim 1 and $A_1$, $A_2$, $A_3$ and $A_4$ are, independently of one another, a C—X group or a nitrogen atom; X being as defined in formula (I) according to claim 1; one of $A_1$, $A_2$, $A_3$ and $A_4$ and at most one of $A_1$, $A_2$, $A_3$ and $A_4$ is a C-q group where q is a halogen atom in the position where the silanyl group should be introduced;

with a silane of formula $SiH(X_1)(X_2)(X_3)$ in which $X_1$, $X_2$ and $X_3$ are as defined in formula (I) according to claim 1;

in the presence of a catalytic amount of a metal complex and of a base in a solvent.

15. A pharmaceutical composition comprising a compound of formula (I) according to claim 1, or a pharmaceutically acceptable acid addition salt thereof in combination with at least one pharmaceutically acceptable excipient.

16. A pharmaceutical composition comprising a compound of formula (I) according to claim 2, or a pharmaceutically acceptable acid addition salt thereof in combination with at least one pharmaceutically acceptable excipient.

17. A pharmaceutical composition comprising a compound of formula (I) according to claim 10, or a pharmaceutically acceptable acid addition salt thereof in combination with at least one pharmaceutically acceptable excipient.

\* \* \* \* \*